(12) United States Patent
Harada et al.

(10) Patent No.: US 7,125,642 B2
(45) Date of Patent: Oct. 24, 2006

(54) SULFONATES, POLYMERS, RESIST COMPOSITIONS AND PATTERNING PROCESS

(75) Inventors: Yuji Harada, Niigata-ken (JP); Jun Hatakeyama, Niigata-ken (JP); Yoshio Kawai, Niigata-ken (JP); Masaru Sasago, Hirakata (JP); Masayuki Endo, Kishiwada (JP); Shinji Kishimura, Itami (JP); Kazuhiko Maeda, Tokyo (JP); Haruhiko Komoriya, Kawagoe (JP); Satoru Miyazawa, Kawagoe (JP)

(73) Assignees: Shin-Etsu Chemical Co., Ltd., Tokyo (JP); Matsushita Electric Industrial Co., Ltd., Kadoma (JP); Central Glass Co., Ltd., Ube (JP)

( * ) Notice: Subject to any disclaimer, the term of this patent is extended or adjusted under 35 U.S.C. 154(b) by 45 days.

(21) Appl. No.: 10/773,340

(22) Filed: Feb. 9, 2004

(65) Prior Publication Data

US 2004/0157156 A1 Aug. 12, 2004

(30) Foreign Application Priority Data

Feb. 10, 2003 (JP) .............................. 2003-032584

(51) Int. Cl.
*G03F 7/004* (2006.01)
*G03F 7/30* (2006.01)
*G03F 7/38* (2006.01)
*C08F 28/02* (2006.01)
*C08F 32/08* (2006.01)
*C08F 12/08* (2006.01)
*C08F 20/02* (2006.01)
*C08F 118/02* (2006.01)
*C08F 216/16* (2006.01)
*C07C 303/26* (2006.01)

(52) U.S. Cl. .................. 430/270.1; 430/326; 430/907; 430/910; 558/44; 558/56; 526/243; 526/281; 526/287; 526/317.1; 526/319; 526/334

(58) Field of Classification Search ............ 430/270.1, 430/325, 326; 526/243, 268, 281, 287, 346; 568/28, 35

See application file for complete search history.

(56) References Cited

U.S. PATENT DOCUMENTS 3,406,004 A * 10/1968 Tesoro et al. .............. 8/115.56
4,491,628 A 1/1985 Ito et al.
5,310,619 A 5/1994 Crivello et al.
2004/0030079 A1* 2/2004 Harada et al. .............. 526/287

FOREIGN PATENT DOCUMENTS

| JP | 63-27829 A | 2/1988 |
|---|---|---|
| JP | 2-27660 B2 | 6/1990 |
| JP | 9-73173 A | 3/1997 |
| JP | 9-230595 A | 9/1997 |
| JP | 10-10739 A | 1/1998 |
| JP | 2001-146505 A | 5/2001 |
| WO | 97-33198 A1 | 9/1997 |

OTHER PUBLICATIONS

CAplus abstract DN 124:87695.*
CAplus abstract DN 113:23058.*
CAplus abstract DN 60:82680 to DE 1163797, Feb. 1964.*
CAplus abstract DN 78:72647.*
Hiroshi, Ito et al., "Polymer design for 157 nm chemically amplified resists", SPIE 2001, Proceedings 4345-31, pp. 273-285.

* cited by examiner

*Primary Examiner*—Rosemary Ashton
(74) *Attorney, Agent, or Firm*—Birch, Stewart, Kolasch & Birch, LLP

(57) ABSTRACT

A sulfonate compound having formula (1) is novel wherein $R^1$ to $R^3$ are H, F or $C_{1-20}$ alkyl or fluoroalkyl, at least one of $R^1$ to $R^3$ contains F. A polymer comprising units derived from the sulfonate compound is used as a base resin to formulate a resist composition which is sensitive to high-energy radiation, maintains high transparency at a wavelength of up to 200 nm, and has improved alkali dissolution contrast and plasma etching resistance

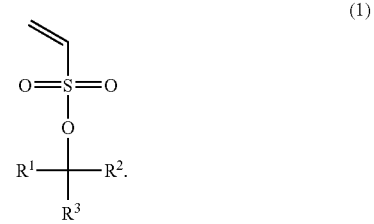

(1)

19 Claims, No Drawings

SULFONATES, POLYMERS, RESIST COMPOSITIONS AND PATTERNING PROCESS

This Nonprovisional application claims priority under 35 U.S.C. § 119(a) on Patent Application No(s). 2003-032584 filed in JAPAN on Feb. 10, 2003, the entire contents of which are hereby incorporated by reference.

This invention relates to polymers useful as the base resin in resist compositions suited for microfabrication and sulfonic acid esters useful as the starting monomers for the polymers. It also relates to resist compositions, especially chemical amplification resist compositions comprising the polymers, and a patterning process using the same.

BACKGROUND OF THE INVENTION

In the drive for higher integration and operating speeds in LSI devices, the pattern rule is made drastically finer. The rapid advance toward finer pattern rules is grounded on the development of a projection lens with an increased NA, a resist material with improved performance, and exposure light of a shorter wavelength. To the demand for a resist material with a higher resolution and sensitivity, chemical amplification positive working resist materials which are catalyzed by acids generated upon light exposure are effective as disclosed in U.S. Pat. Nos. 4,491,628 and 5,310,619 (JP-B 2-27660 and JP-A 63-27829). They now become predominant resist materials especially adapted for deep UV lithography.

Also, the change-over from i-line (365 nm) to shorter wavelength KrF laser (248 nm) brought about a significant innovation. Resist materials adapted for KrF excimer lasers enjoyed early use on the 0.30 micron process, passed through the 0.25 micron rule, and currently entered the mass production phase on the 0.18 micron rule. Engineers have started investigation on the 0.10 micron rule or less, with the trend toward a finer pattern rule being accelerated.

For ArF laser (193 nm), it is expected to enable miniaturization of the design rule to 0.13 μm or less. Since conventionally used novolac resins and polyvinylphenol resins have very strong absorption in proximity to 193 nm, they cannot be used as the base resin for resists. To ensure transparency and dry etching resistance, some engineers investigated acrylic and alicyclic (typically cycloolefin) resins as disclosed in JP-A 9-73173, JP-A 10-10739, JP-A 9-230595 and WO 97/33198.

With respect to $F_2$ laser (157 nm) which is expected to enable further miniaturization to 0.10 μm or less, more difficulty arises in insuring transparency because it was found that acrylic resins which are used as the base resin for ArF are not transmissive to light at all and those cycloolefin resins having carbonyl bonds have strong absorption. It was also found that poly(vinyl phenol) which is used as the base resin for KrF has a window for absorption in proximity to 160 nm, so the transmittance is somewhat improved, but far below the practical level.

Since carbonyl groups and carbon-to-carbon double bonds have absorption in proximity to 157 nm as mentioned above, reducing the number of such units is contemplated to be one effective way for improving transmittance. It was recently found that the transmittance in the $F_2$ region is outstandingly improved by introducing fluorine atoms into base polymers.

It was reported in SPIE 2001, Proceedings 4345-31, "Polymer design for 157 nm chemically amplified resists" that in resist compositions comprising a copolymer of tert-butyl α-trifluoromethylacrylate with 5-(2-hydroxy-2,2-bis-trifluoromethyl)ethyl-2-norbornene and a copolymer of tert-butyl α-trifluoromethylacrylate with 4-(2-hydroxy-2,2-bistrifluoromethyl)methylstyrene, the absorbance of the polymer at 157 nm is improved to about 3. However, these resins are still insufficient in transparency because it is believed that an absorbance of 2 or less is necessary to form a rectangular pattern at a film thickness of at least 2,000 Å through $F_2$ exposure.

The inventor found that incorporating fluorinated vinyl sulfonate units into the above-described α-trifluoromethylacrylate polymers improves the transparency while maintaining the substrate adhesion and developer affinity of the resins. These systems still have an absorbance of approximately 2.

SUMMARY OF THE INVENTION

An object of the invention is to provide a novel polymer having a high transmittance to vacuum ultraviolet radiation of up to 300 nm, especially $F_2$ (157 nm), $Kr_2$ (146 nm), KrAr (134 nm) and $Ar_2$ (126 nm) laser beams, and useful as the base resin in a resist composition, and a novel sulfonic acid ester useful as the starting monomer for the polymer. Another object is to provide a resist composition, especially a chemical amplification resist composition, comprising the polymer, and a patterning process using the same.

It has been found that when a polymer comprising units derived from a monomer having a fluorinated alkyl group introduced on a sulfonate side chain is used as a base resin, the resulting resist composition, especially chemically amplified resist composition is drastically improved in contrast and adhesion without detracting from transparency.

In a first aspect, the present invention provides a sulfonate compound having the following general formula (1).

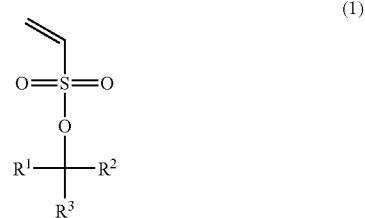

Herein $R^1$ to $R^3$ each are hydrogen, fluorine or a straight, branched or cyclic alkyl or fluorinated alkyl group of 1 to 20 carbon atoms, at least one of $R^1$ to $R^3$ contains fluorine, $R^1$ and $R^2$, $R^1$ and $R^3$, or $R^2$ and $R^3$, taken together, may form a ring, each of $R^1$ to $R^3$ is a straight or branched alkylene or fluorinated alkylene group of 1 to 18 carbon atoms, preferably 1 to 10 carbon atoms, when they form a ring.

In a second aspect, the present invention provides a polymer comprising recurring units of the following general formula (2) and having a weight average molecular weight of 1,000 to 500,000.

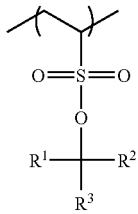
(2)

Herein $R^1$ to $R^3$ are as defined above.

In a preferred embodiment, the polymer further comprises recurring units of at least one type selected from the following general formulae (3a) to (3f).

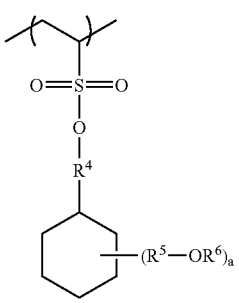
(3a)

(3b)

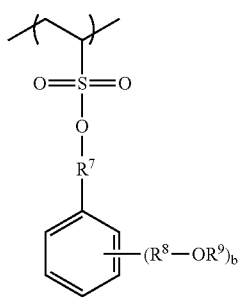
(3c)

(3d)

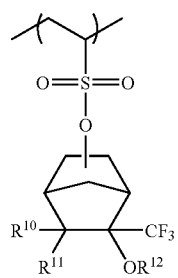

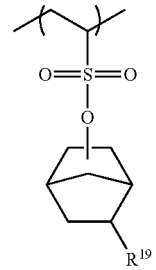
(3e)

(3f)

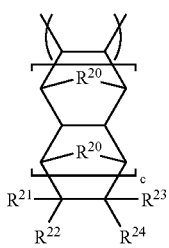

Herein $R^4$, $R^5$, $R^7$, $R^8$ and $R^{15}$ each are a single bond or a straight, branched or cyclic alkylene or fluorinated alkylene group of 1 to 20 carbon atoms, $R^6$, $R^9$, $R^{12}$ and $R^{18}$ each are hydrogen or an acid labile group, $R^{10}$, $R^{11}$, $R^{13}$, $R^{14}$, $R^{16}$ and $R^{17}$ each are hydrogen, fluorine, a straight, branched or cyclic alkyl or fluorinated alkyl group of 1 to 20 carbon atoms, at least one of $R^{16}$ and $R^{17}$ contains at least one fluorine atom, $R^{19}$ is a straight, branched or cyclic fluorinated alkyl group of 1 to 20 carbon atoms, "a" and "b" each are 1 or 2.

In a preferred embodiment, the polymer further comprises recurring units of the following general formula (4).

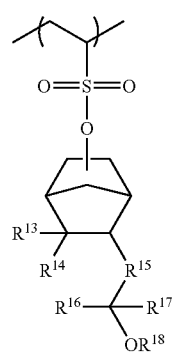
(4)

Herein $R^{20}$ is a methylene group, oxygen atom or sulfur atom, $R^{21}$ to $R^{24}$ each are hydrogen, fluorine, —$R^{25}$—$OR^{26}$, —$R^{25}$—$CO_2R^{26}$ or a straight, branched or cyclic alkyl or fluorinated alkyl group of 1 to 20 carbon atoms, at least one of $R^{21}$ to $R^{24}$ containing —$R^{25}$—$OR^{26}$ or —$R^{25}$—$CO_2R^{26}$, $R^{25}$ is a single bond or a straight, branched or cyclic alkylene or fluorinated alkylene group of 1 to 20 carbon atoms, $R^{26}$ is hydrogen, an acid labile group, adhesive group or a straight, branched or cyclic fluorinated alkyl group of 1 to 20 carbon atoms which may contain a hydrophilic group such as hydroxyl, and c is 0 or 1.

More preferably, the recurring units of formula (4) have a structure of the following general formula (4a) or (4b).

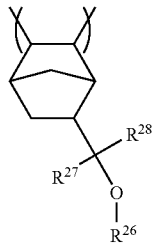
(4a)

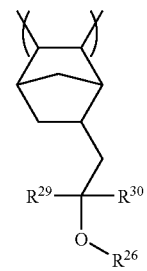
(4b)

Herein $R^{26}$ is as defined above, $R^{27}$ to $R^{30}$ each are hydrogen, fluorine or an alkyl or fluorinated alkyl group of 1 to 4 carbon atoms, at least either one of $R^{27}$ and $R^{28}$ contains at least one fluorine atom, and at least either one of $R^{29}$ and $R^{30}$ contains at least one fluorine atom.

In a preferred embodiment, the polymer further comprises recurring units of the following general formula (5).

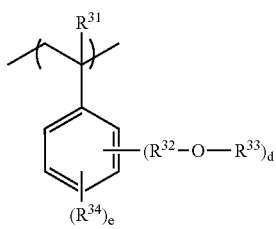
(5)

Herein $R^{31}$ is hydrogen, fluorine or a straight, branched or cyclic alkyl or fluorinated alkyl group of 1 to 20 carbon atoms, $R^{32}$ is a single bond or a straight, branched or cyclic alkylene or fluorinated alkylene group of 1 to 20 carbon atoms, $R^{33}$ is hydrogen or an acid labile group, $R^{34}$ is fluorine or a straight, branched or cyclic fluorinated alkyl group of 1 to 20 carbon atoms, d is 1 or 2, and e is an integer of 0 to 4, satisfying $1 \leq d+e \leq 5$.

More preferably, the recurring units of formula (5) have the following formula (5a) or (5b).

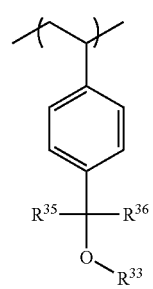
(5a)

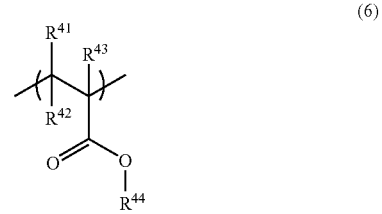
(5b)

Herein $R^{33}$ is as defined above, $R^{35}$ to $R^{40}$ each are hydrogen, fluorine or an alkyl or fluorinated alkyl group of 1 to 4 carbon atoms, at least either one of $R^{35}$ and $R^{36}$ contains at least one fluorine atom, at least either one of $R^{37}$ and $R^{38}$ contains at least one fluorine atom, and at least either one of $R^{39}$ and $R^{40}$ contains at least one fluorine atom.

In another preferred embodiment, the polymer further comprises recurring units of the following general formula (6).

(6)

Herein $R^{41}$ to $R^{43}$ each are hydrogen, fluorine or a straight, branched or cyclic alkyl or fluorinated alkyl group of 1 to 20 carbon atoms, and $R^{44}$ is hydrogen, an acid labile group, an adhesive group or a straight, branched or cyclic fluorinated alkyl group of 1 to 20 carbon atoms which may contain a hydrophilic group such as hydroxyl. Most often $R^{43}$ is trifluoromethyl.

In a third aspect, the present invention provides a resist composition comprising the polymer defined above, and specifically a chemically amplified positive resist composition comprising (A) the polymer defined above, (B) an organic solvent, and (C) a photoacid generator. The resist composition may further comprise (D) a basic compound and/or (E) a dissolution inhibitor.

In a fourth aspect, the present invention provides a process for forming a resist pattern comprising the steps of applying the above resist composition onto a substrate to form a coating; heat treating the coating and then exposing it to high-energy radiation in a wavelength band of 100 to 180 nm or 1 to 30 nm through a photomask; and optionally heat treating the exposed coating and developing it with a developer. The high-energy radiation is typically an $F_2$ laser beam, $Ar_2$ laser beam or soft x-ray.

DESCRIPTION OF THE PREFERRED EMBODIMENTS

Polymer

For improving the transmittance in proximity to 157 nm, reducing the number of carbonyl groups and/or carbon-to-carbon double bonds is contemplated to be one effective way. It was also found that introducing fluorine atoms into base polymers makes a great contribution to improved transmittance. In fact, poly(vinyl phenol) having fluorine introduced in its aromatic rings offers a transmittance nearly on a practically acceptable level (see JP-A 2001-146505). However, this base polymer was found to turn to be negative upon exposure to high-energy radiation as from an $F_2$ laser, interfering with its use as a practical resist. On the other hand, those polymers obtained by introducing fluorine into acrylic resins or polymers containing in their backbone an alicyclic compound originating from a norbornene derivative were found to have a high transparency and eliminate the negative turning problem. However, an increased rate of introduction of fluorine into a resin to enhance the transparency thereof tends to compromise the adhesion of resin to substrate or the penetration of a developer.

It has been found that sulfonates have a relatively high transmittance at about 157 nm despite two sulfur-oxygen double bonds, and a resin comprising such sulfonate units is dramatically improved in substrate adhesion and developer penetration as compared with the aforementioned fluorinated polymers. Specifically, using a base polymer comprising units of the general formula (2) derived from a sulfonate compound of the general formula (1) which is obtained by introducing fluorine into a tertiary alkyl ester of sulfonic acid which inherently lacks stability, a resist composition having an acid eliminating ability is obtained while maintaining stability.

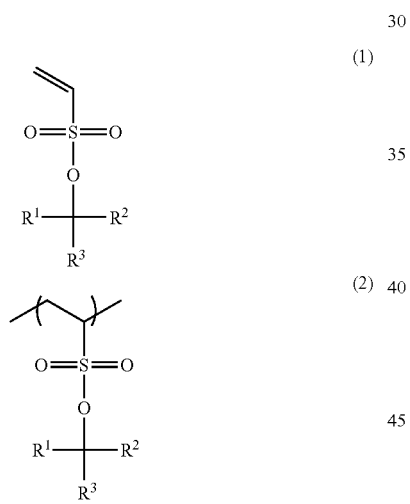

Herein $R^1$ to $R^3$ each are hydrogen, fluorine or a straight, branched or cyclic alkyl or fluorinated alkyl group of 1 to 20 carbon atoms, at least one of $R^1$ to $R^3$ contains fluorine, a pair of $R^1$ and $R^2$, a pair of $R^1$ and $R^3$, or a pair of $R^2$ and $R^3$, taken together, may form a ring, each of $R^1$ to $R^3$ is a straight or branched alkylene or fluorinated alkylene group of 1 to 18 carbon atoms, preferably 1 to 10 carbon atoms, when they form a ring.

While the polymer or high molecular weight compound of the invention is defined as comprising recurring units of the general formula (2), recurring units of at least one type selected from the general formulae (3a) to (3f) and/or recurring units of the general formula (4) and/or recurring units of the general formula (5) and/or recurring units of the general formula (6) are preferably incorporated in order to improve the dissolution contrast, substrate adhesion, dry etching resistance and other properties of the resist.

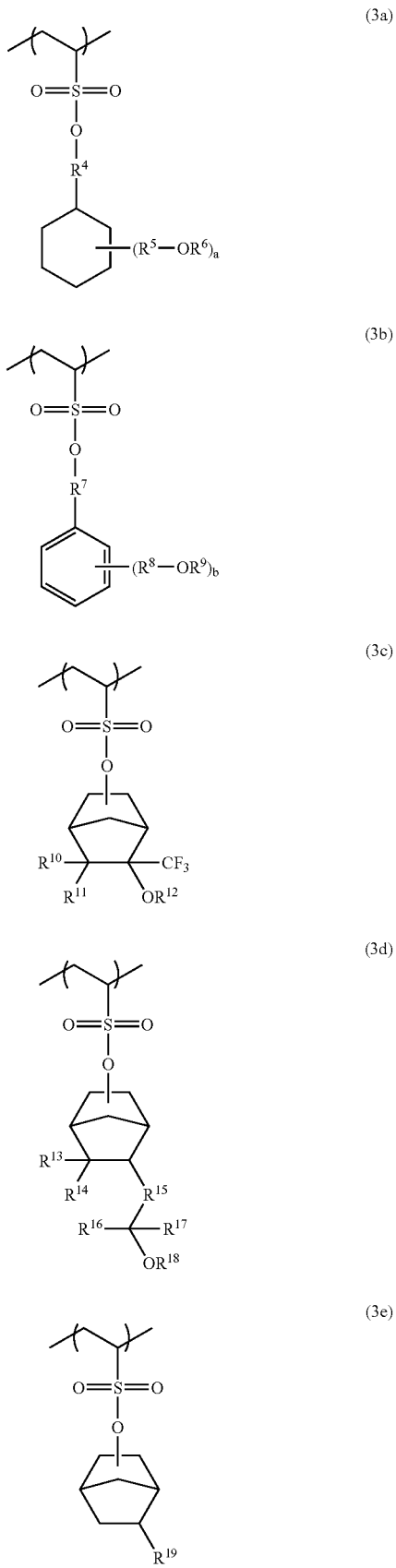

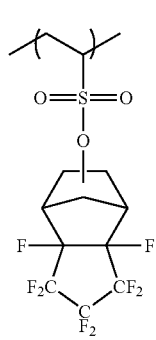
(3f)

Herein $R^4$, $R^5$, $R^7$, $R^8$ and $R^{15}$ each are a single bond or a straight, branched or cyclic alkylene or fluorinated alkylene group of 1 to 20 carbon atoms, $R^6$, $R^9$, $R^{12}$ and $R^{18}$ each are hydrogen or an acid labile group, $R^{10}$, $R^{11}$, $R^{13}$, $R^{14}$, $R^{16}$ and $R^{17}$ each are hydrogen, fluorine, a straight, branched or cyclic alkyl or fluorinated alkyl group of 1 to 20 carbon atoms, at least one of $R^{16}$ and $R^{17}$ contains at least one fluorine atom, $R^{19}$ is a straight, branched or cyclic fluorinated alkyl group of 1 to 20 carbon atoms, "a" and "b" each are 1 or 2.

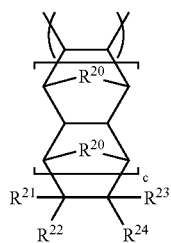
(4)

Herein $R^{20}$ is a methylene group, oxygen atom or sulfur atom, $R^{21}$ to $R^{24}$ each are hydrogen, fluorine, —$R^{25}$—$OR^{26}$, —$R^{25}$—$CO_2R^{26}$ or a straight, branched or cyclic alkyl or fluorinated alkyl group of 1 to 20 carbon atoms, at least one of $R^{21}$ to $R^{24}$ containing —$R^{25}$—$OR^{26}$ or —$R^{25}$—$CO_2R^{26}$, $R^{25}$ is a single bond or a straight, branched or cyclic alkylene or fluorinated alkylene group of 1 to 20 carbon atoms, $R^{26}$ is hydrogen, an acid labile group, adhesive group or a straight, branched or cyclic fluorinated alkyl group of 1 to 20 carbon atoms which may contain a hydrophilic group such as hydroxyl, and c is 0 or 1.

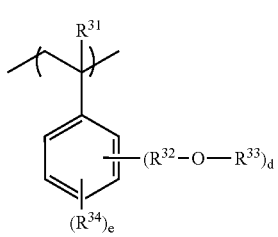
(5)

Herein $R^{31}$ is hydrogen, fluorine or a straight, branched or cyclic alkyl or fluorinated alkyl group of 1 to 20 carbon atoms, $R^{32}$ is a single bond or a straight, branched or cyclic alkylene or fluorinated alkylene group of 1 to 20 carbon atoms, $R^{33}$ is hydrogen or an acid labile group, $R^{34}$ is fluorine or a straight, branched or cyclic fluorinated alkyl group of 1 to 20 carbon atoms, d is 1 or 2, and e is an integer of 0 to 4, satisfying $1 \leq d+e \leq 5$.

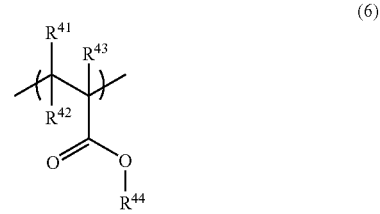
(6)

Herein $R^{41}$ to $R^{43}$ each are hydrogen, fluorine or a straight, branched or cyclic alkyl or fluorinated alkyl group of 1 to 20 carbon atoms, and $R^{44}$ is hydrogen, an acid labile group, an adhesive group or a straight, branched or cyclic fluorinated alkyl group of 1 to 20 carbon atoms which may contain a hydrophilic group such as hydroxyl. Preferably, $R^{43}$ is trifluoromethyl.

The preferred recurring units of formula (4) are units of the following general formula (4a) or (4b).

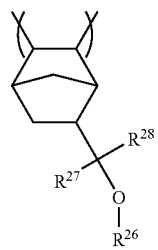
(4a)

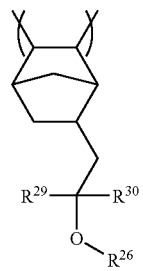
(4b)

Herein $R^{26}$ is as defined above, $R^{27}$ to $R^{30}$ each are hydrogen, fluorine or an alkyl or fluorinated alkyl group of 1 to 4 carbon atoms, at least either one of $R^{27}$ and $R^{28}$ contains at least one fluorine atom, and at least either one of $R^{29}$ and $R^{30}$ contains at least one fluorine atom.

The preferred recurring units of formula (5) are units of the following formula (5a) or (5b).

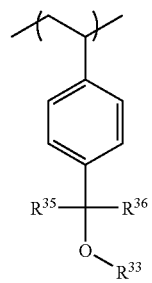

(5a)

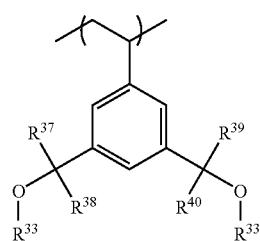

(5b)

Herein $R^{33}$ is as defined above, $R^{35}$ to $R^{40}$ each are hydrogen, fluorine or an alkyl or fluorinated alkyl group of 1 to 4 carbon atoms, at least either one of $R^{35}$ and $R^{36}$ contains at least one fluorine atom, at least either one of $R^{37}$ and $R^{38}$ contains at least one fluorine atom, and at least either one of $R^{39}$ and $R^{40}$ contains at least one fluorine atom.

More particularly, suitable straight, branched or cyclic alkyl groups of 1 to 20 carbon atoms include, but are not limited to, methyl, ethyl, propyl, isopropyl, n-propyl, n-butyl, sec-butyl, tert-butyl, cyclopentyl, cyclohexyl, cyclohexylmethyl, 2-ethylhexyl, n-octyl, 2-adamantyl, and (2-adamantyl)methyl, with those of 1 to 12 carbon atoms, especially 1 to 10 carbon atoms being preferred.

The fluorinated alkyl groups correspond to the foregoing alkyl groups in which some or all of the hydrogen atoms are replaced by fluorine atoms. Examples include, but are not limited to, trifluoromethyl, 2,2,2-trifluoroethyl, 3,3,3-trifluoropropyl, 1,1,1,3,3,3-hexafluoroisopropyl, and 1,1,2,2,3,3,3-heptafluoropropyl as well as groups of the following formulae.

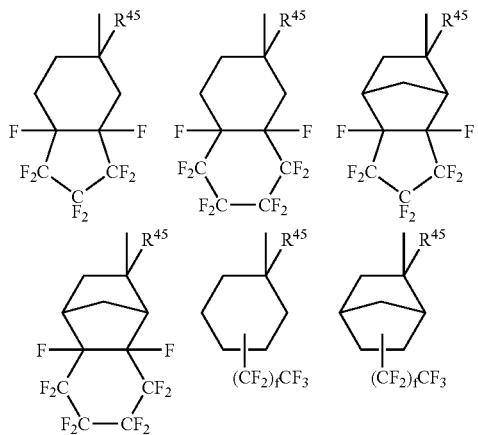

Herein, $R^{45}$ is a hydrogen atom, a fluorine atom or a straight, branched or cyclic alkyl or fluorinated alkyl group of 1 to 10 carbon atoms, and f is an integer of 0 to 5.

Suitable straight, branched or cyclic alkylene groups of 1 to 20 carbon atoms correspond to the foregoing alkyl groups with one hydrogen atom eliminated. Suitable fluorinated alkylene groups are similar alkylene groups which are partially or entirely substituted with fluorine atoms.

The acid labile groups represented by $R^6$, $R^9$, $R^{12}$, $R^{18}$, $R^{26}$, $R^{33}$ and $R^{44}$ are selected from a variety of such groups, preferably from among the groups of the following formulae (7) to (9).

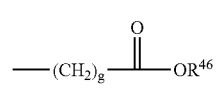

(7)

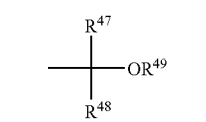

(8)

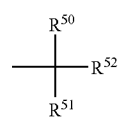

(9)

In formula (7), $R^{46}$ is a tertiary alkyl group of 4 to 20 carbon atoms, preferably 4 to 15 carbon atoms, or an oxoalkyl group of 4 to 20 carbon atoms. Suitable tertiary alkyl groups include tert-butyl, tert-amyl, 1,1-diethylpropyl, 1-ethylcyclopentyl, 1-butylcyclopentyl, 1-ethylcyclohexyl, 1-butylcyclohexyl, 1-ethyl-2-cyclopentenyl, 1-ethyl-2-cyclohexenyl, and 2-methyl-2-adamantyl. Suitable oxoalkyl groups include 3-oxocyclohexyl, 4-methyl-2-oxooxan-4-yl, and 5-methyl-5-oxooxolan-4-yl. Letter g is an integer of 0 to 6.

Illustrative, non-limiting, examples of the acid labile group of formula (7) include tert-butoxycarbonyl, tert-butoxycarbonylmethyl, tert-amyloxycarbonyl, tert-amyloxycarbonylmethyl, 1,1-diethylpropyloxycarbonyl, 1,1-diethylpropyloxycarbonylmethyl, 1-ethylcyclopentyloxycarbonyl, 1-ethylcyclopentyloxycarbonylmethyl, 1-ethyl-2-cyclopentenyloxycarbonyl, 1-ethyl-2-cyclopentenyloxycarbonylmethyl, 1-ethoxyethoxycarbonylmethyl, 2-tetrahydropyranyloxycarbonylmethyl, and 2-tetrahydrofuranyloxycarbonylmethyl groups.

In formula (8), $R^{47}$ and $R^{48}$ are hydrogen or straight, branched or cyclic alkyl groups of 1 to 18 carbon atoms, preferably 1 to 10 carbon atoms, for example, methyl, ethyl, propyl, isopropyl, n-butyl, sec-butyl, tert-butyl, cyclopentyl, cyclohexyl, 2-ethylhexyl and n-octyl. $R^{49}$ is a monovalent hydrocarbon group of 1 to 18 carbon atoms, preferably 1 to 10 carbon atoms, which may contain a hetero atom such as oxygen, for example, straight, branched or cyclic alkyl groups and substituted ones of these alkyl groups in which some hydrogen atoms are substituted with hydroxyl, alkoxy, oxo, amino or alkylamino groups. Exemplary substituted alkyl groups are shown below.

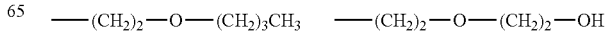

-continued

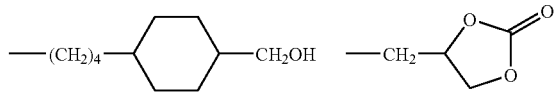

A pair of $R^{47}$ and $R^{48}$, a pair of $R^{47}$ and $R^{49}$, or a pair of $R^{48}$ and $R^{49}$ may bond together to form a ring. Each of $R^{47}$, $R^{48}$ and $R^{49}$ is a straight or branched alkylene group of 1 to 18 carbon atoms, preferably 1 to 10 carbon atoms, when they form a ring.

Of the acid labile groups of formula (8), straight or branched ones are exemplified by the following groups.

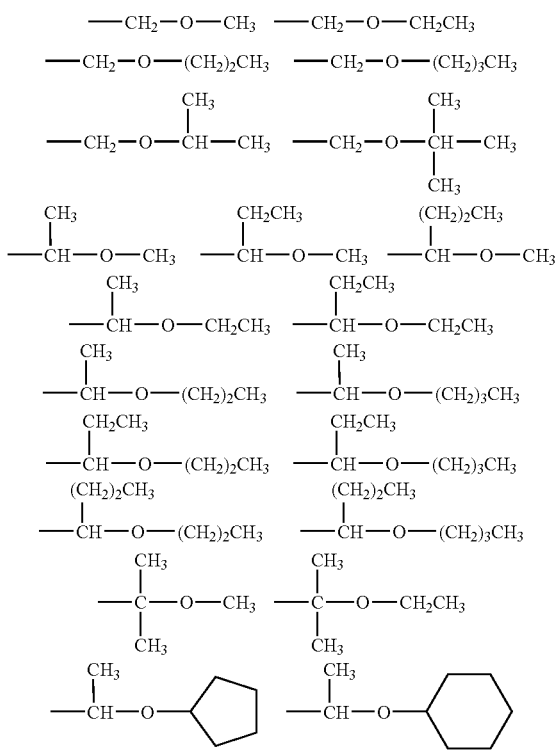

Of the acid labile groups of formula (8), cyclic ones are exemplified by tetrahydrofuran-2-yl, 2-methyltetrahydrofuran-2-yl, tetrahydropyran-2-yl, and 2-methyltetrahydropyran-2-yl.

Of the groups of formula (8), ethoxyethyl, butoxyethyl and ethoxypropyl are preferred.

In formula (9), $R^{50}$, $R^{51}$ and $R^{52}$ each are a monovalent hydrocarbon group, typically a straight, branched or cyclic alkyl group of 1 to 20 carbon atoms, which may contain a hetero atom such as oxygen, sulfur, nitrogen or fluorine. A pair of $R^{50}$ and $R^{51}$, $R^{50}$ and $R^{52}$, and $R^{51}$ and $R^{52}$, taken together, may form a ring with the carbon atom to which they are bonded.

Examples of the tertiary alkyl group represented by formula (9) include tert-butyl, triethylcarbyl, 1-ethylnorbornyl, 1-methylcyclohexyl, 1-ethylcyclopentyl, 2-(2-methyl)adamantyl, 2-(2-ethyl)adamantyl, tert-amyl, 1,1,1,3,3,3-hexafluoro-2-methyl-isopropyl, and 1,1,1,3,3,3-hexafluoro-2-cyclohexyl-isopropyl as well as the groups shown below.

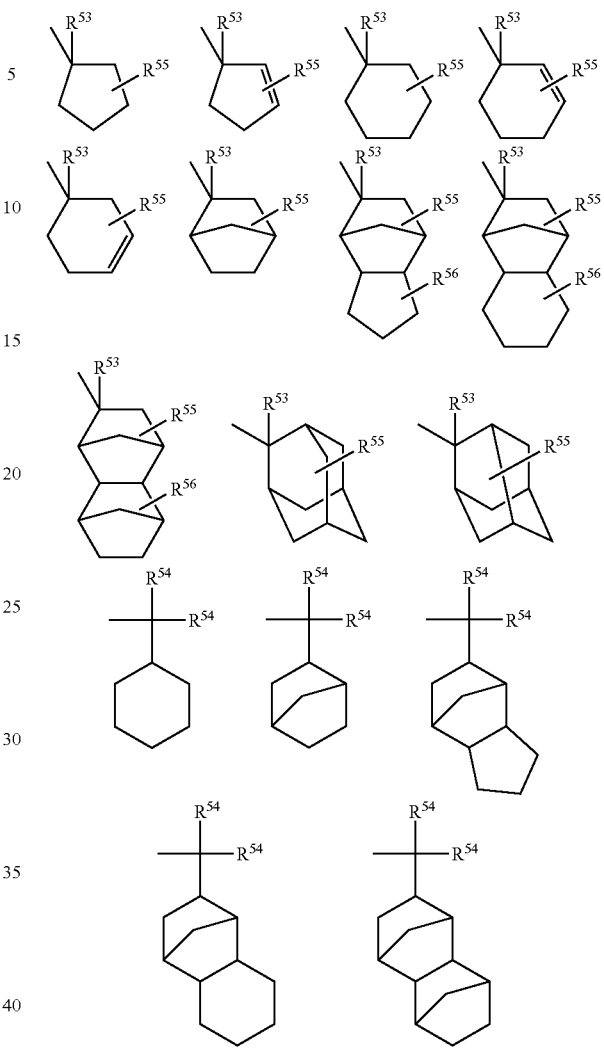

Herein, $R^{53}$ is a straight, branched or cyclic alkyl group of 1 to 6 carbon atoms, such as methyl, ethyl, propyl, isopropyl, n-butyl, sec-butyl, n-pentyl, n-hexyl, cyclopropyl, cyclopropylmethyl, cyclobutyl, cyclopentyl and cyclohexyl. $R^{54}$ is a straight, branched or cyclic alkyl group of 2 to 6 carbon atoms, such as ethyl, propyl, isopropyl, n-butyl, sec-butyl, n-pentyl, n-hexyl, cyclopropyl, cyclopropylmethyl, cyclobutyl, cyclopentyl and cyclohexyl. Each of $R^{55}$ and $R^{56}$ is hydrogen, a monovalent hydrocarbon group of 1 to 6 carbon atoms which may contain a hetero atom, or a monovalent hydrocarbon group of 1 to 6 carbon atoms which may be separated by a hetero atom. These groups may be straight, branched or cyclic. The hetero atom is typically selected from oxygen, sulfur and nitrogen atoms and may be contained or intervene in the form of —OH, —OR$^{57}$, —O—, —S—, —S(=O)—, —NH$_2$, —NHR$^{57}$, —N(R$^{57}$)$_2$, —NH— or —NR$^{57}$— wherein $R^{57}$ is a $C_{1-5}$ alkyl group. Examples of $R^{55}$ and $R^{56}$ groups include methyl, hydroxymethyl, ethyl, hydroxyethyl, propyl, isopropyl, n-butyl, sec-butyl, n-pentyl, n-hexyl, methoxy, methoxymethoxy, ethoxy and tert-butoxy.

Next, the adhesive groups represented by $R^{26}$ and $R^{44}$ are selected from a variety of such groups, preferably from among the groups of the following formulae.

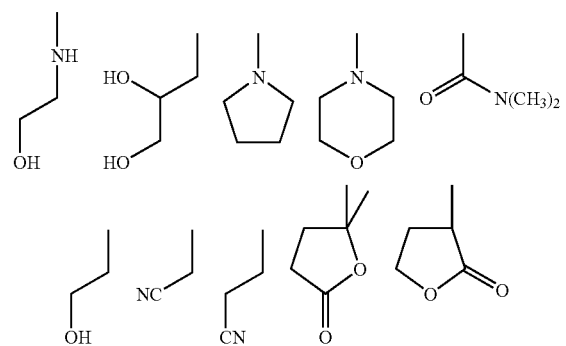
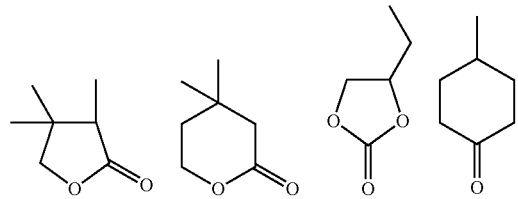
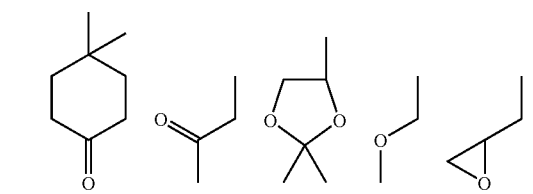
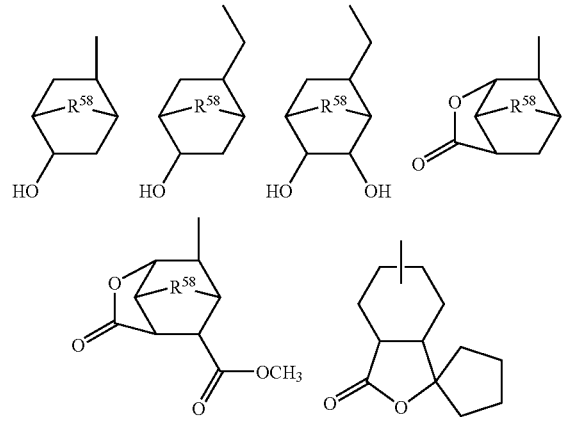
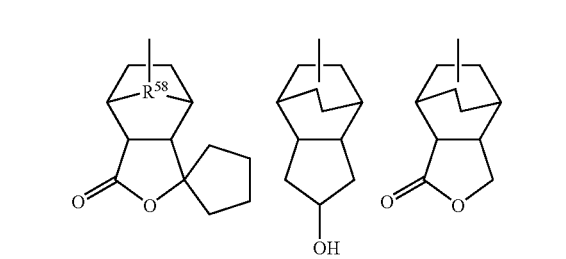
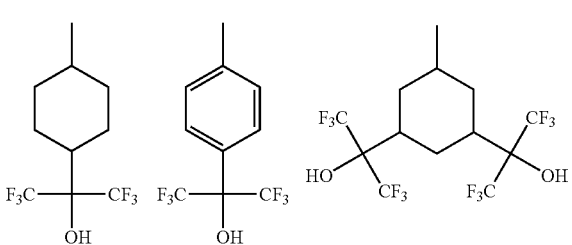
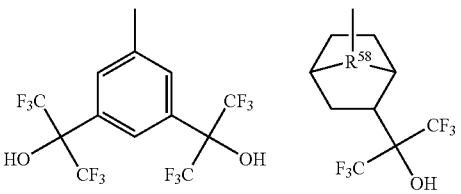
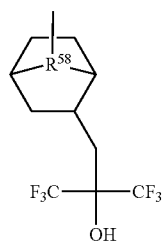
Herein, $R^{58}$ is a methylene group, oxygen atom or sulfur atom.
Illustrative examples of the units of formula (2) are given below, though not limited thereto.
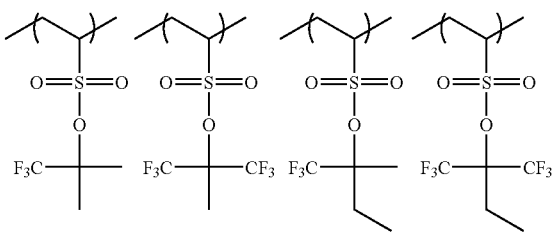
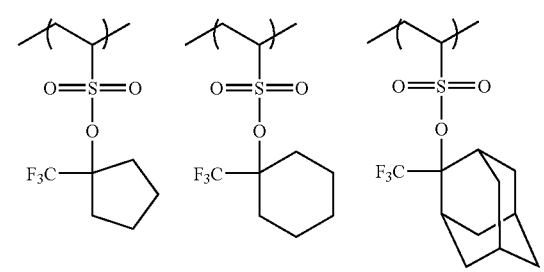
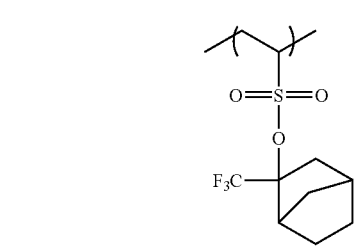
Illustrative examples of the units of formulae (3a) to (3d) are given below, though not limited thereto.

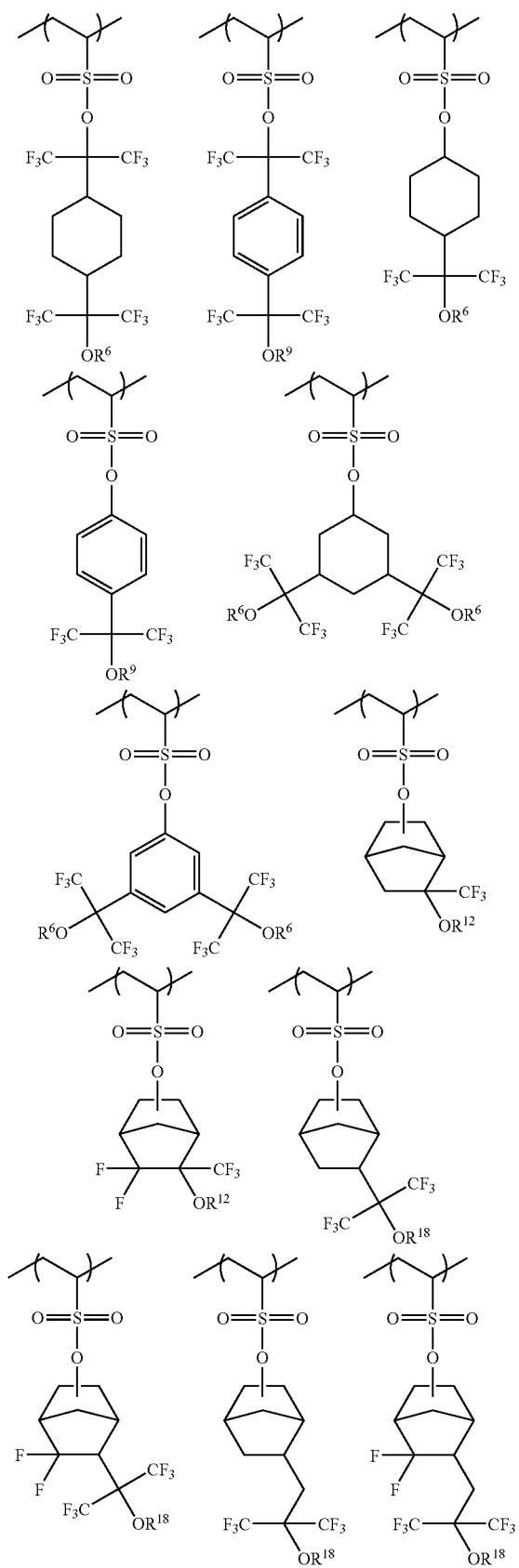
Herein $R^6$, $R^9$ and $R^{18}$ are as defined above.
Illustrative examples of the units of formulae (4), (4a) and (4b) are given below, though not limited thereto.
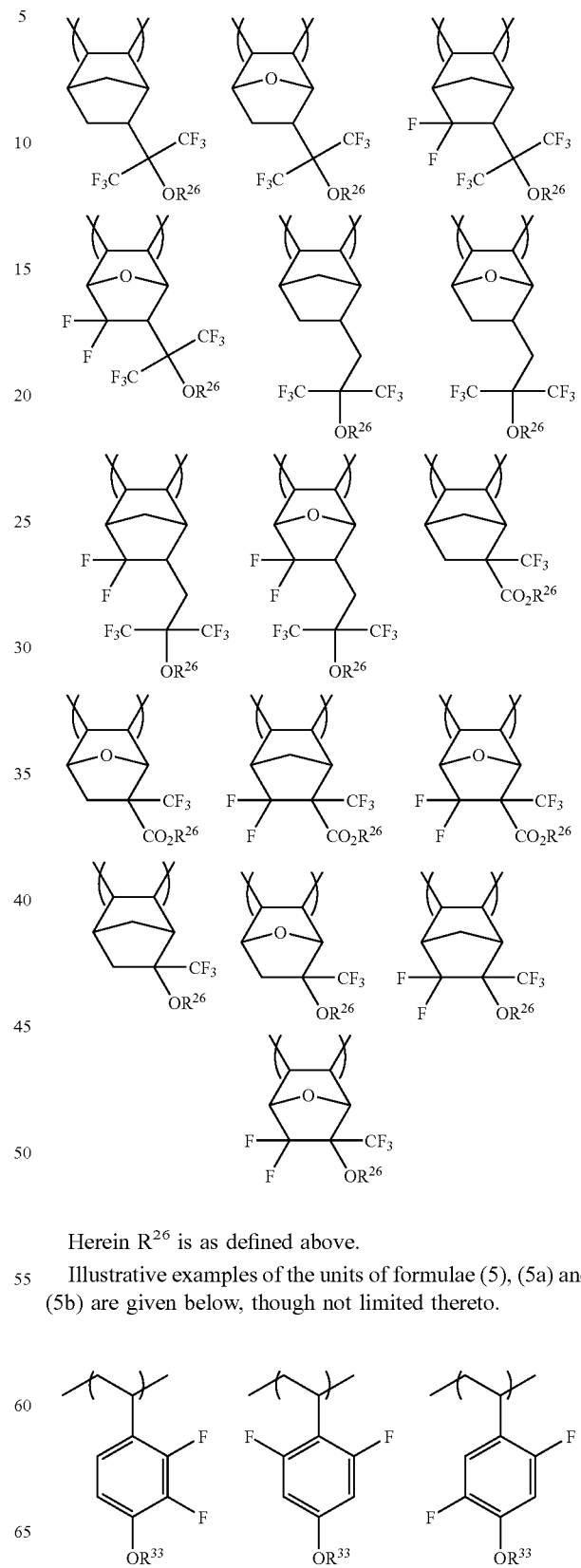
Herein $R^{26}$ is as defined above.
Illustrative examples of the units of formulae (5), (5a) and (5b) are given below, though not limited thereto.
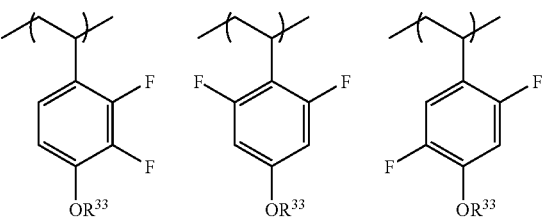

-continued

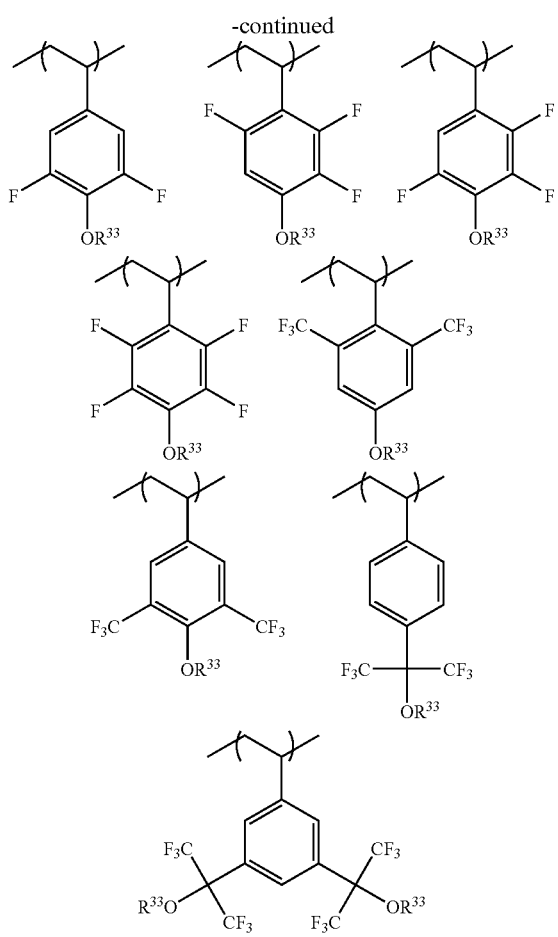

Herein R³³ is as defined above.

Besides, units as shown below may be incorporated in the inventive polymers for the purpose of improving substrate adhesion and transparency.

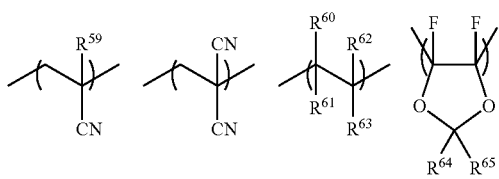

Herein, $R^{59}$ to $R^{63}$ each are hydrogen, fluorine or a fluorinated alkyl group of 1 to 4 carbon atoms, and at least one of $R^{60}$ to $R^{63}$ contains at least one fluorine atom. $R^{64}$ and $R^{65}$ each are hydrogen, methyl or trifluoromethyl.

In the inventive polymers wherein U1 represents units of formula (2), U2 represents units of formulae (3a) to (3f), U3 represents units of formulae (4), (4a) and (4b), U4 represents units of formulae (5), (5a) and (5b), U5 represents units of formula (6), and U6 represents adhesive and transparent units other than the foregoing, and U1+U2+U3+U4+U5+U6=1, U's are preferably in the range:

$0 < U1 \leq 0.9$, more preferably $0.1 \leq U1 \leq 0.5$,
$0 \leq U2 \leq 0.6$, more preferably $0 \leq U2 \leq 0.4$,
$0 \leq U3 \leq 0.6$, more preferably $0 \leq U3 \leq 0.4$,
$0 \leq U4 \leq 0.6$, more preferably $0 \leq U4 \leq 0.4$,
$0 \leq U5 \leq 0.7$, more preferably $0 \leq U5 \leq 0.5$, and
$0 \leq U6 \leq 0.4$, more preferably $0 \leq U6 \leq 0.2$.

The polymers of the invention are generally synthesized by dissolving monomers corresponding to the respective units of formulae (2), (3a) to (3f), (4), (4a), (4b), (5), (5a), (5b) and (6) and optionally, an adhesion-improving monomer, a transparency-improving monomer and the like in a solvent, adding a catalyst thereto, and effecting polymerization reaction while heating or cooling the system if necessary. The polymerization reaction depends on the type of initiator or catalyst, trigger means (including light, heat, radiation and plasma), and polymerization conditions (including temperature, pressure, concentration, solvent, and additives). Commonly used for preparation of the polymers of the invention are radical copolymerization of triggering polymerization with initiators such as 2,2'-azobisisobutyronitrile (AIBN) or the like, and ion (anion) polymerization using catalysts such as alkyl lithium. These polymerization steps may be carried out in their conventional manner.

The radical polymerization initiator used herein is not critical. Exemplary initiators include azo compounds such as AIBN, 2,2'-azobis(4-methoxy-2,4-dimethylvaleronitrile), 2,2'-azobis(2,4-dimethylvaleronitrile), and 2,2'-azobis(2,4,4-trimethylpentane); peroxide compounds such as tert-butyl peroxypivalate, lauroyl peroxide, benzoyl peroxide and tert-butyl peroxylaurate; water-soluble initiators, for example, persulfate salts such as potassium persulfate; and redox combinations of potassium persulfate or peroxides such as hydrogen peroxide with reducing agents such as sodium sulfite. The amount of the polymerization initiator used is determined as appropriate in accordance with such factors as the identity of initiator and polymerization conditions, although the amount is often in the range of about 0.001 to 5% by weight, especially about 0.01 to 2% by weight based on the total weight of monomers to be polymerized.

For the polymerization reaction, a solvent may be used. The polymerization solvent used herein is preferably one which does not interfere with the polymerization reaction. Typical solvents include ester solvents such as ethyl acetate and n-butyl acetate, ketone solvents such as acetone, methyl ethyl ketone and methyl isobutyl ketone, aliphatic or aromatic hydrocarbon solvents such as toluene, xylene and cyclohexane, alcohol solvents such as isopropyl alcohol and ethylene glycol monomethyl ether, and ether solvents such as diethyl ether, dioxane, and tetrahydrofuran. These solvents may be used alone or in admixture of two or more. Further, any of well-known molecular weight modifiers such as dodecylmercaptan may be used in the polymerization system.

The temperature of polymerization reaction varies in accordance with the identity of polymerization initiator and the boiling point of the solvent although it is often preferably in the range of about 20 to 200° C., and especially about 50 to 140° C. Any desired reactor or vessel may be used for the polymerization reaction.

From the solution or dispersion of the polymer thus obtained, the organic solvent or water serving as the reaction medium is removed by any of well-known techniques. Suitable techniques include, for example, re-precipitation followed by filtration, and heat distillation under vacuum.

Desirably the polymer has a weight average molecular weight of about 1,000 to about 500,000, and especially about 2,000 to about 100,000.

The polymer of the invention can be used as a base resin in resist compositions, specifically chemical amplification type resist compositions, and especially chemical amplification type positive working resist compositions. It is understood that the polymer of the invention may be admixed with another polymer for the purpose of altering the dynamic properties, thermal properties, alkali solubility and other physical properties of polymer film. The type of the other polymer which can be admixed is not critical. Any of polymers known to be useful in resist use may be admixed in any desired proportion.

In the practice of the invention, the sulfonate compounds of the formula (1) can be prepared by the following scheme, although their preparation is not limited thereto.

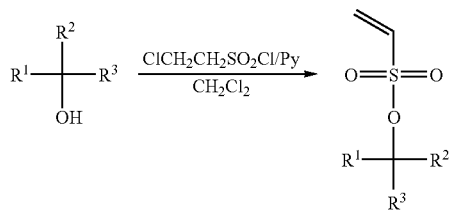

Herein $R^1$ to $R^3$ are as defined above.

The reaction readily takes place under well-known conditions. Preferably, the alcohol reactant and a base such as pyridine are simultaneously added to a solvent such as dichloromethane, and chloroethanesulfonyl chloride is added dropwise under ice cooling. The desired monomer is obtained in this way.

Resist Composition

As long as the polymer of the invention is used as a base resin, the resist composition of the invention may be prepared using well-known components. In a preferred embodiment, the chemically amplified positive resist composition is defined as comprising (A) the above-defined polymer as a base resin, (B) an organic solvent, and (C) a photoacid generator. In the resist composition, there may be further formulated (D) a basic compound and/or (E) a dissolution inhibitor.

Component (B)

The organic solvent used as component (B) in the invention may be any organic solvent in which the base resin, photoacid generator, and other components are soluble. Illustrative, non-limiting, examples of the organic solvent include ketones such as cyclohexanone and methyl-2-n-amylketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate, propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; and lactones such as γ-butyrolactone.

Also useful are fluorinated organic solvents. Illustrative, non-limiting examples include 2-fluoroanisole, 3-fluoroanisole, 4-fluoroanisole, 2,3-difluoroanisole, 2,4-difluoroanisole, 2,5-difluoroanisole, 5,8-difluoro-1,4-benzodioxane, 2,3-difluorobenzyl alcohol, 1,3-difluoro-2-propanol, 2',4'-difluoropropiophenone, 2,4-difluorotoluene, trifluoroacetaldehyde ethyl hemiacetal, trifluoroacetamide, trifluoroethanol, 2,2,2-trifluorobutyrate, ethylheptafluoroethanol, ethyl heptafluorobutylacetate, ethyl hexafluoroglutarylmethyl, ethyl 3-hydroxy-4,4,4-trifluoroacetoacetate, ethyl pentafluoropropynylacetate, ethyl perfluorooctanoate, ethyl 4,4,4-trifluoroacetoacetate, ethyl 4,4,4-trifluorobutyrate, ethyl 4,4,4-trifluorocrotonate, ethyl trifluoropyruvate, sec-ethyl trifluoroacetate, fluorocyclohexane, 2,2,3,3,4,4,4-heptafluoro-1-butanol, 1,1,1,2,2,3,3-heptafluoro-7,7-dimethyl-4,6-octanedione, 1,1,1,3,5,5,5-heptafluoropentane-2,4-dione, 3,3,4,4,5,5,5-heptafluoro-2-pentanol, 3,3,4,4,5,5,5-heptafluoro-2-pentanone, isopropyl 4,4,4-trifluoroacetoacetate, methyl perfluorodecanoate, methyl perfluoro(2-methyl-3-oxahexanoate), methyl perfluorononanoate, methyl perfluorooctanoate, methyl 2,3,3,3-tetrafluoropropionate, methyl trifluoroacetoacetate, 1,1,1,2,2,6,6,6-octafluoro-2,4-hexanedione, 2,2,3,3,4,4,5,5-octafluoro-1-pentanol, 1H,1H,2H,2H-perfluoro-1-decanol, perfluoro-2,5-dimethyl-3,6-dioxane anionic acid methyl ester, 2H-perfluoro-5-methyl-3,6-dioxanonane, 1H,1H,2H,3H,3H-perfluorononane-1,2-diol, 1H,1H,9H-perfluoro-1-nonanol, 1H,1H-perfluorooctanol, 1H,1H,2H,2H-perfluorooctanol, 2H-perfluoro-5,8,11,14-tetramethyl-3,6,9,12,15-pentaoxaoctadecane, perfluorotributylamine, perfluorotrihexylamine, perfluoro-2,5,8-trimethyl-3,6,9,12,15-pentaoxaoctadecane, perfluorotributylamine, perfluorotrihexylamine, methyl perfluoro-2,5,8-trimethyl-3,6,9-trioxadodecanoate, perfluorotripentylamine, perfluorotriisopropylamine, 1H,1H,2H,3H,3H-perfluoroundecane-1,2-diol, trifluorobutanol, 1,1,1-trifluoro-5-methyl-2,4-hexanedione, 1,1,1-trifluoro-2-propanol, 3,3,3-trifluoro-1-propanol, 1,1,1-trifluoro-2-propyl acetate, perfluorobutyltetrahydrofuran, perfluorodecalin, perfluoro(1,2-dimethylcyclohexane), perfluoro(1,3-dimethylcyclohexane), propylene glycol trifluoromethyl ether acetate, propylene glycol methyl ether trifluoromethyl acetate, butyl trifluoromethylacetate, methyl 3-trifluoromethoxypropionate, perfluorocyclohexane, propylene glycol trifluoromethyl ether, butyl trifluoroacetate, and 1,1,1-trifluoro-5,5-dimethyl-2,4-hexanedione.

These solvents may be used alone or in combinations of two or more thereof. Of the above organic solvents, preferred are diethylene glycol dimethyl ether and 1-ethoxy-2-propanol, in which the photoacid generator is most soluble, and propylene glycol monomethyl ether acetate which is safe, and mixtures thereof.

The solvent is preferably used in an amount of about 300 to 10,000 parts by weight, more preferably about 500 to 5,000 parts by weight per 100 parts by weight of the base resin.

Component (C)

The photoacid generator is a compound capable of generating an acid upon exposure to high energy radiation or electron beams and includes the following:
(i) onium salts of the formula (P1a-1), (P1a-2) or (P1b),
(ii) diazomethane derivatives of the formula (P2),
(iii) glyoxime derivatives of the formula (P3),
(iv) bissulfone derivatives of the formula (P4),
(v) sulfonic acid esters of N-hydroxyimide compounds of the formula (P5),
(vi) β-ketosulfonic acid derivatives,
(vii) disulfone derivatives,
(viii) nitrobenzylsulfonate derivatives, and
(ix) sulfonate derivatives.

These photoacid generators are described in detail.

(i) Onium Salts of Formula (P1a-1), (P1a-2) or (P1b):

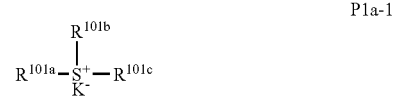

-continued

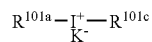

Herein, $R^{101a}$, $R^{101b}$, and $R^{101c}$ independently represent straight, branched or cyclic alkyl, alkenyl, oxoalkyl or oxoalkenyl groups of 1 to 12 carbon atoms, aryl groups of 6 to 20 carbon atoms, or aralkyl or aryloxoalkyl groups of 7 to 12 carbon atoms, wherein some or all of the hydrogen atoms may be replaced by alkoxy or other groups. Also, $R^{101b}$ and $R^{101c}$, taken together, may form a ring. $R^{101b}$ and $R^{101c}$ each are alkylene groups of 1 to 6 carbon atoms when they form a ring. $K^-$ is a non-nucleophilic counter ion.

$R^{101a}$, $R^{101b}$, and $R^{101c}$ may be the same or different and are illustrated below. Exemplary alkyl groups include methyl, ethyl, propyl, isopropyl, n-butyl, sec-butyl, tert-butyl, pentyl, hexyl, heptyl, octyl, cyclopentyl, cyclohexyl, cycloheptyl, cyclopropylmethyl, 4-methylcyclohexyl, cyclohexylmethyl, norbornyl, and adamantyl. Exemplary alkenyl groups include vinyl, allyl, propenyl, butenyl, hexenyl, and cyclohexenyl. Exemplary oxoalkyl groups include 2-oxocyclopentyl and 2-oxocyclohexyl as well as 2-oxopropyl, 2-cyclopentyl-2-oxoethyl, 2-cyclohexyl-2-oxoethyl, and 2-(4-methylcyclohexyl)-2-oxoethyl. Exemplary aryl groups include phenyl and naphthyl; alkoxyphenyl groups such as p-methoxyphenyl, m-methoxyphenyl, o-methoxyphenyl, ethoxyphenyl, p-tert-butoxyphenyl, and m-tert-butoxyphenyl; alkylphenyl groups such as 2-methylphenyl, 3-methylphenyl, 4-methylphenyl, ethylphenyl, 4-tert-butylphenyl, 4-butylphenyl, and dimethylphenyl; alkylnaphthyl groups such as methylnaphthyl and ethylnaphthyl; alkoxynaphthyl groups such as methoxynaphthyl and ethoxynaphthyl; dialkylnaphthyl groups such as dimethylnaphthyl and diethylnaphthyl; and dialkoxynaphthyl groups such as dimethoxynaphthyl and diethoxynaphthyl. Exemplary aralkyl groups include benzyl, phenylethyl, and phenethyl. Exemplary aryloxoalkyl groups are 2-aryl-2-oxoethyl groups such as 2-phenyl-2-oxoethyl, 2-(1-naphthyl)-2-oxoethyl, and 2-(2-naphthyl)-2-oxoethyl. Examples of the non-nucleophilic counter ion represented by $K^-$ include halide ions such as chloride and bromide ions, fluoroalkylsulfonate ions such as triflate, 1,1,1-trifluoroethanesulfonate, and nonafluorobutanesulfonate, arylsulfonate ions such as tosylate, benzenesulfonate, 4-fluorobenzenesulfonate, and 1,2,3,4,5-pentafluorobenzenesulfonate, and alkylsulfonate ions such as mesylate and butanesulfonate.

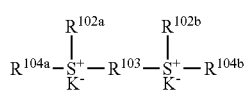

Herein, $R^{102a}$ and $R^{102b}$ independently represent straight, branched or cyclic alkyl groups of 1 to 8 carbon atoms. $R^{103}$ represents a straight, branched or cyclic alkylene group of 1 to 10 carbon atoms. $R^{104a}$ and $R^{104b}$ independently represent 2-oxoalkyl groups of 3 to 7 carbon atoms. $K^-$ is a non-nucleophilic counter ion.

Illustrative of the groups represented by $R^{102a}$ and $R^{102b}$ are methyl, ethyl, propyl, isopropyl, n-butyl, sec-butyl, tert-butyl, pentyl, hexyl, heptyl, octyl, cyclopentyl, cyclohexyl, cyclopropylmethyl, 4-methylcyclohexyl, and cyclohexylmethyl. Illustrative of the groups represented by $R^{103}$ are methylene, ethylene, propylene, butylene, pentylene, hexylene, heptylene, octylene, nonylene, 1,4-cyclohexylene, 1,2-cyclohexylene, 1,3-cyclopentylene, 1,4-cyclooctylene, and 1,4-cyclohexanedimethylene. Illustrative of the groups represented by $R^{104a}$ and $R^{104b}$ are 2-oxopropyl, 2-oxocyclopentyl, 2-oxocyclohexyl, and 2-oxocycloheptyl. Illustrative examples of the counter ion represented by $K^-$ are the same as exemplified for formulae (P1a-1) and (P1a-2).

(ii) Diazomethane Derivatives of Formula (P2)

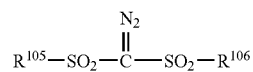

Herein, $R^{105}$ and $R^{106}$ independently represent straight, branched or cyclic alkyl or halogenated alkyl groups of 1 to 12 carbon atoms, aryl or halogenated aryl groups of 6 to 20 carbon atoms, or aralkyl groups of 7 to 12 carbon atoms.

Of the groups represented by $R^{105}$ and $R^{106}$, exemplary alkyl groups include methyl, ethyl, propyl, isopropyl, n-butyl, sec-butyl, tert-butyl, pentyl, hexyl, heptyl, octyl, amyl, cyclopentyl, cyclohexyl, cycloheptyl, norbornyl, and adamantyl. Exemplary halogenated alkyl groups include trifluoromethyl, 1,1,1-trifluoroethyl, 1,1,1-trichloroethyl, and nonafluorobutyl. Exemplary aryl groups include phenyl; alkoxyphenyl groups such as p-methoxyphenyl, m-methoxyphenyl, o-methoxyphenyl, ethoxyphenyl, p-tert-butoxyphenyl, and m-tert-butoxyphenyl; and alkylphenyl groups such as 2-methylphenyl, 3-methylphenyl, 4-methylphenyl, ethylphenyl, 4-tert-butylphenyl, 4-butylphenyl, and dimethylphenyl. Exemplary halogenated aryl groups include fluorophenyl, chlorophenyl, and 1,2,3,4,5-pentafluorophenyl. Exemplary aralkyl groups include benzyl and phenethyl.

(iii) Glyoxime Derivatives of Formula (P3)

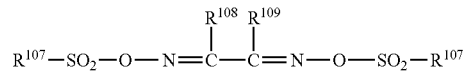

Herein, $R^{107}$, $R^{108}$, and $R^{109}$ independently represent straight, branched or cyclic alkyl or halogenated alkyl groups of 1 to 12 carbon atoms, aryl or halogenated aryl groups of 6 to 20 carbon atoms, or aralkyl groups of 7 to 12 carbon atoms. Also, $R^{108}$ and $R^{109}$, taken together, may form a ring. $R^{108}$ and $R^{109}$ each are straight or branched alkylene groups of 1 to 6 carbon atoms when they form a ring.

Illustrative examples of the alkyl, halogenated alkyl, aryl, halogenated aryl, and aralkyl groups represented by $R^{107}$, $R^{108}$, and $R^{109}$ are the same as exemplified for $R^{105}$ and $R^{106}$. Examples of the alkylene groups represented by $R^{108}$ and $R^{109}$ include methylene, ethylene, propylene, butylene, and hexylene.

(iv) Bissulfone Derivatives of Formula (P4)

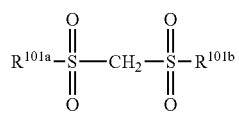

Herein, $R^{101a}$ and $R^{101b}$ are as defined above.

(v) Sulfonic Acid Esters of N-hydroxyimide Compounds of Formula (P5)

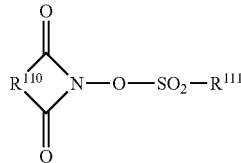

Herein, $R^{110}$ is an arylene group of 6 to 10 carbon atoms, alkylene group of 1 to 6 carbon atoms, or alkenylene group of 2 to 6 carbon atoms wherein some or all of the hydrogen atoms may be replaced by straight or branched alkyl or alkoxy groups of 1 to 4 carbon atoms, nitro, acetyl, or phenyl groups. $R^{111}$ is a straight, branched or cyclic alkyl group of 1 to 8 carbon atoms, alkenyl, alkoxyalkyl, phenyl or naphthyl group wherein some or all of the hydrogen atoms may be replaced by alkyl or alkoxy groups of 1 to 4 carbon atoms, phenyl groups (which may have substituted thereon an alkyl or alkoxy of 1 to 4 carbon atoms, nitro, or acetyl group), hetero-aromatic groups of 3 to 5 carbon atoms, or chlorine or fluorine atoms.

Of the groups represented by $R^{110}$, exemplary arylene groups include 1,2-phenylene and 1,8-naphthylene; exemplary alkylene groups include methylene, ethylene, trimethylene, tetramethylene, phenylethylene, and norbornane-2,3-diyl; and exemplary alkenylene groups include 1,2-vinylene, 1-phenyl-1,2-vinylene, and 5-norbornene-2,3-diyl. Of the groups represented by $R^{111}$, exemplary alkyl groups are as exemplified for $R^{101a}$ to $R^{101e}$; exemplary alkenyl groups include vinyl, 1-propenyl, allyl, 1-butenyl, 3-butenyl, isoprenyl, 1-pentenyl, 3-pentenyl, 4-pentenyl, dimethylallyl, 1-hexenyl, 3-hexenyl, 5-hexenyl, 1-heptenyl, 3-heptenyl, 6-heptenyl, and 7-octenyl; and exemplary alkoxyalkyl groups include methoxymethyl, ethoxymethyl, propoxymethyl, butoxymethyl, pentyloxymethyl, hexyloxymethyl, heptyloxymethyl, methoxyethyl, ethoxyethyl, propoxyethyl, butoxyethyl, pentyloxyethyl, hexyloxyethyl, methoxypropyl, ethoxypropyl, propoxypropyl, butoxypropyl, methoxybutyl, ethoxybutyl, propoxybutyl, methoxypentyl, ethoxypentyl, methoxyhexyl, and methoxyheptyl.

Of the substituents on these groups, the alkyl groups of 1 to 4 carbon atoms include methyl, ethyl, propyl, isopropyl, n-butyl, isobutyl and tert-butyl; the alkoxy groups of 1 to 4 carbon atoms include methoxy, ethoxy, propoxy, isopropoxy, n-butoxy, isobutoxy, and tert-butoxy; the phenyl groups which may have substituted thereon an alkyl or alkoxy of 1 to 4 carbon atoms, nitro, or acetyl group include phenyl, tolyl, p-tert-butoxyphenyl, p-acetylphenyl and p-nitrophenyl; the hetero-aromatic groups of 3 to 5 carbon atoms include pyridyl and furyl.

Illustrative examples of the photoacid generator include: onium salts such as
diphenyliodonium trifluoromethanesulfonate,
(p-tert-butoxyphenyl)phenyliodonium trifluoromethanesulfonate,
diphenyliodonium p-toluenesulfonate,
(p-tert-butoxyphenyl)phenyliodonium p-toluenesulfonate,
triphenylsulfonium trifluoromethanesulfonate,
(p-tert-butoxyphenyl)diphenylsulfonium trifluoromethanesulfonate,
bis(p-tert-butoxyphenyl)phenylsulfonium trifluoromethanesulfonate,
tris(p-tert-butoxyphenyl)sulfonium trifluoromethanesulfonate,
triphenylsulfonium p-toluenesulfonate, (p-tert-butoxyphenyl)diphenylsulfonium p-toluenesulfonate,
bis(p-tert-butoxyphenyl)phenylsulfonium p-toluenesulfonate,
tris(p-tert-butoxyphenyl)sulfonium p-toluenesulfonate,
triphenylsulfonium nonafluorobutanesulfonate,
triphenylsulfonium butanesulfonate,
trimethylsulfonium trifluoromethanesulfonate,
trimethylsulfonium p-toluenesulfonate,
cyclohexylmethyl(2-oxocyclohexyl)sulfonium trifluoromethanesulfonate,
cyclohexylmethyl(2-oxocyclohexyl)sulfonium p-toluenesulfonate,
dimethylphenylsulfonium trifluoromethanesulfonate,
dimethylphenylsulfonium p-toluenesulfonate,
dicyclohexylphenylsulfonium trifluoromethanesulfonate,
dicyclohexylphenylsulfonium p-toluenesulfonate,
trinaphthylsulfonium trifluoromethanesulfonate,
cyclohexylmethyl(2-oxocyclohexyl)sulfonium trifluoromethanesulfonate,
(2-norbornyl)methyl(2-oxocyclohexyl)sulfonium trifluoromethanesulfonate,
ethylenebis[methyl(2-oxocyclopentyl)sulfonium trifluoromethanesulfonate], and
1,2'-naphthylcarbonylmethyltetrahydrothiophenium triflate;
diazomethane derivatives such as
bis(benzenesulfonyl)diazomethane,
bis(p-toluenesulfonyl)diazomethane,
bis(xylenesulfonyl)diazomethane,
bis(cyclohexylsulfonyl)diazomethane,
bis(cyclopentylsulfonyl)diazomethane,
bis(n-butylsulfonyl)diazomethane,
bis(isobutylsulfonyl)diazomethane,
bis(sec-butylsulfonyl)diazomethane,
bis(n-propylsulfonyl)diazomethane,
bis(isopropylsulfonyl)diazomethane,
bis(tert-butylsulfonyl)diazomethane,
bis(n-amylsulfonyl)diazomethane,
bis(isoamylsulfonyl)diazomethane,
bis(sec-amylsulfonyl)diazomethane,
bis(tert-amylsulfonyl)diazomethane,
1-cyclohexylsulfonyl-1-(tert-butylsulfonyl)diazomethane,
1-cyclohexylsulfonyl-1-(tert-amylsulfonyl)diazomethane, and
1-tert-amylsulfonyl-1-(tert-butylsulfonyl)diazomethane;
glyoxime derivatives such as
bis-O-(p-toluenesulfonyl)-α-dimethylglyoxime,
bis-O-(p-toluenesulfonyl)-α-diphenylglyoxime,
bis-O-(p-toluenesulfonyl)-α-dicyclohexylglyoxime,
bis-O-(p-toluenesulfonyl)-2,3-pentanedioneglyoxime,
bis-O-(p-toluenesulfonyl)-2-methyl-3,4-pentanedioneglyoxime,
bis-O-(n-butanesulfonyl)-α-dimethylglyoxime,
bis-O-(n-butanesulfonyl)-α-diphenylglyoxime,
bis-O-(n-butanesulfonyl)-α-dicyclohexylglyoxime,
bis-O-(n-butanesulfonyl)-2,3-pentanedioneglyoxime,
bis-O-(n-butanesulfonyl)-2-methyl-3,4-pentanedioneglyoxime,
bis-O-(methanesulfonyl)-α-dimethylglyoxime,
bis-O-(trifluoromethanesulfonyl)-α-dimethylglyoxime,
bis-O-(1,1,1-trifluoroethanesulfonyl)-α-dimethylglyoxime,
bis-O-(tert-butanesulfonyl)-α-dimethylglyoxime,
bis-O-(perfluorooctanesulfonyl)-α-dimethylglyoxime,
bis-O-(cyclohexanesulfonyl)-α-dimethylglyoxime,
bis-O-(benzenesulfonyl)-α-dimethylglyoxime, bis-O-(p-fluorobenzenesulfonyl)-α-dimethylglyoxime,
bis-O-(p-tert-butylbenzenesulfonyl)-α-dimethylglyoxime,
bis-O-(xylenesulfonyl)-α-dimethylglyoxime, and
bis-O-(camphorsulfonyl)-α-dimethylglyoxime;
  bissulfone derivatives such as
bisnaphthylsulfonylmethane, bistrifluoromethylsulfonylmethane,
bismethylsulfonylmethane, bisethylsulfonylmethane,
bispropylsulfonylmethane, bisisopropylsulfonylmethane,
bis-p-toluenesulfonylmethane, and bisbenzenesulfonylmethane;
  β-ketosulfone derivatives such as
2-cyclohexylcarbonyl-2-(p-toluenesulfonyl)propane and
2-isopropylcarbonyl-2-(p-toluenesulfonyl)propane;
  nitrobenzyl sulfonate derivatives such as
2,6-dinitrobenzyl p-toluenesulfonate and
2,4-dinitrobenzyl p-toluenesulfonate;
  sulfonic acid ester derivatives such as
1,2,3-tris(methanesulfonyloxy)benzene,
1,2,3-tris(trifluoromethanesulfonyloxy)benzene, and
1,2,3-tris(p-toluenesulfonyloxy)benzene; and
  sulfonic acid esters of N-hydroxyimides such as
N-hydroxysuccinimide methanesulfonate,
N-hydroxysuccinimide trifluoromethanesulfonate,
N-hydroxysuccinimide ethanesulfonate,
N-hydroxysuccinimide 1-propanesulfonate,
N-hydroxysuccinimide 2-propanesulfonate,
N-hydroxysuccinimide 1-pentanesulfonate,
N-hydroxysuccinimide 1-octanesulfonate,
N-hydroxysuccinimide p-toluenesulfonate,
N-hydroxysuccinimide p-methoxybenzenesulfonate,
N-hydroxysuccinimide 2-chloroethanesulfonate,
N-hydroxysuccinimide benzenesulfonate,
N-hydroxysuccinimide 2,4,6-trimethylbenzenesulfonate,
N-hydroxysuccinimide 1-naphthalenesulfonate,
N-hydroxysuccinimide 2-naphthalenesulfonate,
N-hydroxy-2-phenylsuccinimide methanesulfonate,
N-hydroxymaleimide methanesulfonate,
N-hydroxymaleimide ethanesulfonate,
N-hydroxy-2-phenylmaleimide methanesulfonate,
N-hydroxyglutarimide methanesulfonate,
N-hydroxyglutarimide benzenesulfonate,
N-hydroxyphthalimide methanesulfonate,
N-hydroxyphthalimide benzenesulfonate,
N-hydroxyphthalimide trifluoromethanesulfonate,
N-hydroxyphthalimide p-toluenesulfonate,
N-hydroxynaphthalimide methanesulfonate,
N-hydroxynaphthalimide benzenesulfonate,
N-hydroxy-5-norbornene-2,3-dicarboxyimide methanesulfonate,
N-hydroxy-5-norbornene-2,3-dicarboxyimide trifluoromethanesulfonate, and
N-hydroxy-5-norbornene-2,3-dicarboxyimide p-toluenesulfonate.

Preferred among these photoacid generators are onium salts such as triphenylsulfonium trifluoromethanesulfonate, (p-tert-butoxyphenyl)diphenylsulfonium trifluoromethanesulfonate,
tris(p-tert-butoxyphenyl)sulfonium trifluoromethanesulfonate,
triphenylsulfonium p-toluenesulfonate,
(p-tert-butoxyphenyl)diphenylsulfonium p-toluenesulfonate,
tris(p-tert-butoxyphenyl)sulfonium p-toluenesulfonate,
trinaphthylsulfonium trifluoromethanesulfonate,
cyclohexylmethyl(2-oxocyclohexyl)sulfonium trifluoromethanesulfonate,
(2-norbornyl)methyl(2-oxocylohexyl)sulfonium trifluoromethanesulfonate, and
1,2'-naphthylcarbonylmethyltetrahydrothiophenium triflate;

diazomethane derivatives such as
bis(benzenesulfonyl)diazomethane,
bis(p-toluenesulfonyl)diazomethane,
bis(cyclohexylsulfonyl)diazomethane,
bis(n-butylsulfonyl)diazomethane,
bis(isobutylsulfonyl)diazomethane,
bis(sec-butylsulfonyl)diazomethane,
bis(n-propylsulfonyl)diazomethane,
bis(isopropylsulfonyl)diazomethane, and
bis(tert-butylsulfonyl)diazomethane;

glyoxime derivatives such as
bis-O-(p-toluenesulfonyl)-α-dimethylglyoxime and
bis-O-(n-butanesulfonyl)-α-dimethylglyoxime;

bissulfone derivatives such as
bisnaphthylsulfonylmethane; and sulfonic acid esters of N-hydroxyimide compounds such as
N-hydroxysuccinimide methanesulfonate,
N-hydroxysuccinimide trifluoromethanesulfonate,
N-hydroxysuccinimide 1-propanesulfonate,
N-hydroxysuccinimide 2-propanesulfonate,
N-hydroxysuccinimide 1-pentanesulfonate,
N-hydroxysuccinimide p-toluenesulfonate,
N-hydroxynaphthalimide methanesulfonate, and
N-hydroxynaphthalimide benzenesulfonate.

These photoacid generators may be used singly or in combinations of two or more thereof. Onium salts are effective for improving rectangularity, while diazomethane derivatives and glyoxime derivatives are effective for reducing standing waves. The combination of an onium salt with a diazomethane or a glyoxime derivative allows for fine adjustment of the profile.

The photoacid generator is added in an amount of 0.1 to 50 parts, and especially 0.5 to 40 parts by weight, per 100 parts by weight of the base resin (all parts are by weight, hereinafter). Less than 0.1 part of the photoacid generator may generate a less amount of acid upon exposure, sometimes leading to a poor sensitivity and resolution whereas more than 50 parts of the photoacid generator may adversely affect transmittance and resolution.

Component (D)

The basic compound used as component (D) is preferably a compound capable of suppressing the rate of diffusion when the acid generated by the photoacid generator diffuses within the resist film. The inclusion of this type of basic compound holds down the rate of acid diffusion within the resist film, resulting in better resolution. In addition, it suppresses changes in sensitivity following exposure, thus reducing substrate and environment dependence, as well as improving the exposure latitude and the pattern profile.

Examples of suitable basic compounds include primary, secondary, and tertiary aliphatic amines, mixed amines, aromatic amines, heterocyclic amines, carboxyl group-bearing nitrogenous compounds, sulfonyl group-bearing nitrogenous compounds, hydroxyl group-bearing nitrogenous compounds, hydroxyphenyl group-bearing nitrogenous compounds, alcoholic nitrogenous compounds, amide derivatives, and imide derivatives.

Examples of suitable primary aliphatic amines include ammonia, methylamine, ethylamine, n-propylamine, isopropylamine, n-butylamine, iso-butylamine, sec-butylamine, tert-butylamine, pentylamine, tert-amylamine, cyclopentylamine, hexylamine, cyclohexylamine, heptylamine, octylamine, nonylamine, decylamine, dodecylamine, cetylamine, methylenediamine, ethylenediamine, and tetraethylenepentamine. Examples of suitable secondary aliphatic amines include dimethylamine, diethylamine, di-n-propylamine, di-iso-propylamine, di-n-butylamine, di-iso-butylamine, di-sec-butylamine, dipentylamine, dicyclopentylamine, dihexylamine, dicyclohexylamine, diheptylamine, dioctylamine, dinonylamine, didecylamine, didodecylamine, dicetylamine, N,N-dimethylmethylenediamine, N,N-dimethylethylenediamine, and N,N-dimethyltetraethylenepentamine. Examples of suitable tertiary aliphatic amines include trimethylamine, triethylamine, tri-n-propylamine, tri-iso-propylamine, tri-n-butylamine, tri-iso-butylamine, tri-sec-butylamine, tripentylamine, tricyclopentylamine, trihexylamine, tricyclohexylamine, triheptylamine, trioctylamine, trinonylamine, tridecylamine, tridodecylamine, tricetylamine, N,N,N',N'-tetramethylmethylenediamine, N,N,N',N'-tetramethylethylenediamine, and N,N,N',N'-tetramethyltetraethylenepentamine.

Examples of suitable mixed amines include dimethylethylamine, methylethylpropylamine, benzylamine, phenethylamine, and benzyldimethylamine. Examples of suitable aromatic amines include aniline derivatives (e.g., aniline, N-methylaniline, N-ethylaniline, N-propylaniline, N,N-dimethylaniline, 2-methylaniline, 3-methylaniline, 4-methylaniline, ethylaniline, propylaniline, trimethylaniline, 2-nitroaniline, 3-nitroaniline, 4-nitroaniline, 2,4-dinitroaniline, 2,6-dinitroaniline, 3,5-dinitroaniline, and N,N-dimethyltoluidine), diphenyl(p-tolyl)amine, methyldiphenylamine, triphenylamine, phenylenediamine, naphthylamine, and diaminonaphthalene. Examples of suitable heterocyclic amines include pyrrole derivatives (e.g., pyrrole, 2H-pyrrole, 1-methylpyrrole, 2,4-dimethylpyrrole, 2,5-dimethylpyrrole, and N-methylpyrrole), oxazole derivatives (e.g., oxazole and isooxazole), thiazole derivatives (e.g., thiazole and isothiazole), imidazole derivatives (e.g., imidazole, 4-methylimidazole, and 4-methyl-2-phenylimidazole), pyrazole derivatives, furazan derivatives, pyrroline derivatives (e.g., pyrroline and 2-methyl-1-pyrroline), pyrrolidine derivatives (e.g., pyrrolidine, N-methylpyrrolidine, pyrrolidinone, and N-methylpyrrolidone), imidazoline derivatives, imidazolidine derivatives, pyridine derivatives (e.g., pyridine, methylpyridine, ethylpyridine, propylpyridine, butylpyridine, 4-(1-butylpentyl)pyridine, dimethylpyridine, trimethylpyridine, triethylpyridine, phenylpyridine, 3-methyl-2-phenylpyridine, 4-tert-butylpyridine, diphenylpyridine, benzylpyridine, methoxypyridine, butoxypyridine, dimethoxypyridine, 1-methyl-2-pyridone, 4-pyrrolidinopyridine, 1-methyl-4-phenylpyridine, 2-(1-ethylpropyl)pyridine, aminopyridine, and dimethylaminopyridine), pyridazine derivatives, pyrimidine derivatives, pyrazine derivatives, pyrazoline derivatives, pyrazolidine derivatives, piperidine derivatives, piperazine derivatives, morpholine derivatives, indole derivatives, isoindole derivatives, 1H-indazole derivatives, indoline derivatives, quinoline derivatives (e.g., quinoline and 3-quinolinecarbonitrile), isoquinoline derivatives, cinnoline derivatives, quinazoline derivatives, quinoxaline derivatives, phthalazine derivatives, purine derivatives, pteridine derivatives, carbazole derivatives, phenanthridine derivatives, acridine derivatives, phenazine derivatives, 1,10-phenanthroline derivatives, adenine derivatives, adenosine derivatives, guanine derivatives, guanosine derivatives, uracil derivatives, and uridine derivatives.

Examples of suitable carboxyl group-bearing nitrogenous compounds include aminobenzoic acid, indolecarboxylic acid, and amino acid derivatives (e.g., nicotinic acid, alanine, arginine, aspartic acid, glutamic acid, glycine, histidine, isoleucine, glycylleucine, leucine, methionine, phenylalanine, threonine, lysine, 3-aminopyrazine-2-carboxylic acid, and methoxyalanine).

Examples of suitable sulfonyl group-bearing nitrogenous compounds include 3-pyridinesulfonic acid and pyridinium p-toluenesulfonate.

Examples of suitable hydroxyl group-bearing nitrogenous compounds, hydroxyphenyl group-bearing nitrogenous compounds, and alcoholic nitrogenous compounds include 2-hydroxypyridine, aminocresol, 2,4-quinolinediol, 3-indolemethanol hydrate, monoethanolamine, diethanolamine, triethanolamine, N-ethyldiethanolamine, N,N-diethylethanolamine, triisopropanolamine, 2,2'-iminodiethanol, 2-aminoethanol, 3-amino-1-propanol, 4-amino-1-butanol, 4-(2-hydroxyethyl)morpholine, 2-(2-hydroxyethyl)pyridine, 1-(2-hydroxyethyl)piperazine, 1-[2-(2-hydroxyethoxy)ethyl]piperazine, piperidine ethanol, 1-(2-hydroxyethyl)pyrrolidine, 1-(2-hydroxyethyl)-2-pyrrolidinone, 3-piperidino-1,2-propanediol, 3-pyrrolidino-1,2-propanediol, 8-hydroxyjulolidine, 3-quinuclidinol, 3-tropanol, 1-methyl-2-pyrrolidine ethanol, 1-aziridine ethanol, N-(2-hydroxyethyl)phthalimide, and N-(2-hydroxyethyl)isonicotinamide.

Examples of suitable amide derivatives include formamide, N-methylformamide, N,N-dimethylformamide, acetamide, N-methylacetamide, N,N-dimethylacetamide, propionamide, and benzamide. Suitable imide derivatives include phthalimide, succinimide, and maleimide.

In addition, basic compounds of the following general formula (B)-1 may also be included alone or in admixture.

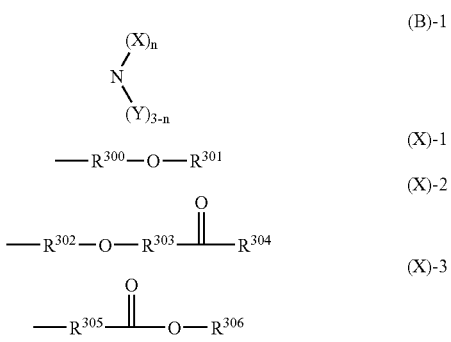

In the formulas, n is 1, 2 or 3. The side chain X may be the same or different and is represented by the formula (X)-1, (X)-2 or (X)-3. The side chain Y may be the same or different and stands for hydrogen or a straight, branched or cyclic alkyl group of 1 to 20 carbon atoms which may contain an ether or hydroxyl group. Two or three X's may bond together to form a ring.

In the formulas, $R^{300}$, $R^{302}$ and $R^{305}$ are independently straight or branched alkylene groups of 1 to 4 carbon atoms; $R^{301}$ and $R^{304}$ are independently hydrogen, straight, branched or cyclic alkyl groups of 1 to 20 carbon atoms, which may contain at least one hydroxyl group, ether, ester or lactone ring; and $R^{303}$ is a single bond or a straight or branched alkylene group of 1 to 4 carbon atoms; and $R^{306}$ is a straight, branched or cyclic alkyl group of 1 to 20 carbon atoms, which may contain at least one hydroxyl group, ether, ester or lactone ring.

Illustrative, non-limiting examples of the compounds of formula (B)-1 include tris(2-methoxymethoxyethyl)amine, tris{2-(2-methoxyethoxy)ethyl}amine, tris{2-(2-methoxyethoxymethoxy)ethyl}amine, tris{2-(1-methoxyethoxy)

ethyl}amine, tris{2-(1-ethoxyethoxy)ethyl}amine, tris{2-(1-ethoxypropoxy)ethyl}amine, tris[2-{2-(2-hydroxyethoxy)ethoxy}ethyl]amine, 4,7,13,16,21,24-hexaoxa-1,10-diazabicyclo[8.8.8]hexacosane, 4,7,13,18-tetraoxa-1,10-diazabicyclo[8.5.5]eicosane, 1,4,10,13-tetraoxa-7,16-diazabicyclooctadecane, 1-aza-12-crown-4, 1-aza-15-crown-5, 1-aza-18-crown-6, tris(2-formyloxyethyl)amine, tris(2-acetoxyethyl)amine, tris(2-propionyloxyethyl)amine, tris(2-butyryloxyethyl)amine, tris(2-isobutyryloxyethyl)amine, tris(2-valeryloxyethyl)amine, tris(2-pivaloyloxyethyl)amine, N,N-bis(2-acetoxyethyl)-2-(acetoxyacetoxy)ethylamine, tris(2-methoxycarbonyloxyethyl)amine, tris(2-tert-butoxycarbonyloxyethyl)amine, tris[2-(2-oxopropoxy)ethyl]amine, tris[2-(methoxycarbonylmethyl)oxyethyl]amine, tris[2-(tert-butoxycarbonylmethyloxy)ethyl]amine, tris[2-(cyclohexyloxycarbonylmethyloxy)ethyl]amine, tris(2-methoxycarbonylethyl)amine, tris(2-ethoxycarbonylethyl)amine, N,N-bis(2-hydroxyethyl)-2-(methoxycarbonyl)ethylamine, N,N-bis(2-acetoxyethyl)-2-(methoxycarbonyl)ethylamine, N,N-bis(2-hydroxyethyl)-2-(ethoxycarbonyl)ethylamine, N,N-bis(2-acetoxyethyl)-2-(ethoxycarbonyl)ethylamine, N,N-bis(2-hydroxyethyl)-2-(2-methoxyethoxycarbonyl)ethylamine, N,N-bis(2-acetoxyethyl)-2-(2-methoxyethoxycarbonyl)ethylamine, N,N-bis(2-hydroxyethyl)-2-(2-hydroxyethoxycarbonyl)ethylamine, N,N-bis(2-acetoxyethyl)-2-(2-acetoxyethoxycarbonyl)ethylamine, N,N-bis(2-hydroxyethyl)-2-[(methoxycarbonyl)methoxycarbonyl]ethylamine, N,N-bis(2-acetoxyethyl)-2-[(methoxycarbonyl)methoxycarbonyl]ethylamine, N,N-bis(2-hydroxyethyl)-2-(2-oxopropoxycarbonyl)ethylamine, N,N-bis(2-acetoxyethyl)-2-(2-oxopropoxycarbonyl)ethylamine, N,N-bis(2-hydroxyethyl)-2-(tetrahydrofurfuryloxycarbonyl)ethylamine, N,N-bis(2-acetoxyethyl)-2-(tetrahydrofurfuryloxycarbonyl)ethylamine, N,N-bis(2-hydroxyethyl)-2-[(2-oxotetrahydrofuran-3-yl)oxycarbonyl]ethylamine, N,N-bis(2-acetoxyethyl)-2-[(2-oxotetrahydrofuran-3-yl)oxycarbonyl]ethylamine, N,N-bis(2-hydroxyethyl)-2-(4-hydroxybutoxycarbonyl)ethylamine, N,N-bis(2-formyloxyethyl)-2-(4-formyloxybutoxycarbonyl)ethylamine, N,N-bis(2-formyloxyethyl)-2-(2-formyloxyethoxycarbonyl)ethylamine, N,N-bis(2-methoxyethyl)-2-(methoxycarbonyl)ethylamine, N-(2-hydroxyethyl)-bis[2-(methoxycarbonyl)ethyl]amine, N-(2-acetoxyethyl)-bis[2-(methoxycarbonyl)ethyl]amine, N-(2-hydroxyethyl)-bis[2-(ethoxycarbonyl)ethyl]amine, N-(2-acetoxyethyl)-bis[2-(ethoxycarbonyl)ethyl]amine, N-(3-hydroxy-1-propyl)-bis[2-(methoxycarbonyl)ethyl]amine, N-(3-acetoxy-1-propyl)-bis[2-(methoxycarbonyl)ethyl]amine, N-(2-methoxyethyl)-bis[2-(methoxycarbonyl)ethyl]amine, N-butyl-bis[2-(methoxycarbonyl)ethyl]amine, N-butyl-bis[2-(2-methoxyethoxycarbonyl)ethyl]amine, N-methyl-bis(2-acetoxyethyl)amine, N-ethyl-bis(2-acetoxyethyl)amine, N-methyl-bis(2-pivaloyloxyethyl)amine, N-ethyl-bis[2-(methoxycarbonyloxy)ethyl]amine, N-ethyl-bis[2-(tert-butoxycarbonyloxy)ethyl]amine, tris(methoxycarbonylmethyl)amine, N-butyl-tris(ethoxycarbonylmethyl)amine, N-butyl-bis(methoxycarbonylmethyl)amine, N-hexyl-bis(methoxycarbonylmethyl)amine, and β-(diethylamino)-δ-valerolactone.

Also useful are one or more of cyclic structure-bearing basic compounds having the following general formula (B)-2.

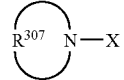

(B)-2

Herein X is as defined above, and $R^{307}$ is a straight or branched alkylene group of 2 to 20 carbon atoms which may contain one or more carbonyl, ether, ester or sulfide groups.

Illustrative examples of the cyclic structure-bearing basic compounds having formula (B)-2 include 1-[2-(methoxymethoxy)ethyl]pyrrolidine, 1-[2-(methoxymethoxy)ethyl]piperidine, 4-[2-(methoxymethoxy)ethyl]morpholine, 1-[2-[(2-methoxyethoxy)methoxy]ethyl]pyrrolidine, 1-[2-[(2-methoxyethoxy)methoxy]ethyl]piperidine, 4-[2-[(2-methoxyethoxy)methoxy]ethyl]morpholine, 2-(1-pyrrolidinyl)ethyl acetate, 2-piperidinoethyl acetate, 2-morpholinoethyl acetate, 2-(1-pyrrolidinyl)ethyl formate, 2-piperidinoethyl propionate, 2-morpholinoethyl acetoxyacetate, 2-(1-pyrrolidinyl)ethyl methoxyacetate, 4-[2-(methoxycarbonyloxy)ethyl]morpholine, 1-[2-(t-butoxycarbonyloxy)ethyl]piperidine, 4-[2-(2-methoxyethoxycarbonyloxy)ethyl]morpholine, methyl 3-(1-pyrrolidinyl)propionate, methyl 3-piperidinopropionate, methyl 3-morpholinopropionate, methyl 3-(thiomorpholino)propionate, methyl 2-methyl-3-(1-pyrrolidinyl)propionate, ethyl 3-morpholinopropionate, methoxycarbonylmethyl 3-piperidinopropionate, 2-hydroxyethyl 3-(1-pyrrolidinyl)propionate, 2-acetoxyethyl 3-morpholinopropionate, 2-oxotetrahydrofuran-3-yl 3-(1-pyrrolidinyl)propionate, tetrahydrofurfuryl 3-morpholinopropionate, glycidyl 3-piperidinopropionate, 2-methoxyethyl 3-morpholinopropionate, 2-(2-methoxyethoxy)ethyl 3-(1-pyrrolidinyl)propionate, butyl 3-morpholinopropionate, cyclohexyl 3-piperidinopropionate, α-(1-pyrrolidinyl)methyl-γ-butyrolactone, β-piperidino-γ-butyrolactone, β-morpholino-δ-valerolactone, methyl 1-pyrrolidinylacetate, methyl piperidinoacetate, methyl morpholinoacetate, methyl thiomorpholinoacetate, ethyl 1-pyrrolidinylacetate, and 2-methoxyethyl morpholinoacetate.

Also, one or more of cyano-bearing basic compounds having the following general formulae (B)-3 to (B)-6 may be blended.

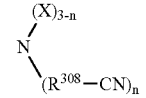

(B)-3

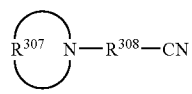

(B)-4

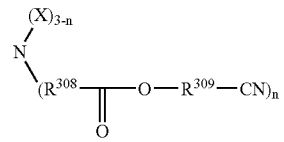

(B)-5

-continued

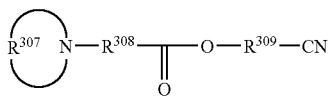
(B)-6

Herein, X, $R^{307}$ and n are as defined above, and $R^{308}$ and $R^{309}$ each are independently a straight or branched alkylene group of 1 to 4 carbon atoms.

Illustrative examples of the cyano-bearing basic compounds include 3-(diethylamino)propiononitrile, N,N-bis(2-hydroxyethyl)-3-aminopropiononitrile, N,N-bis(2-acetoxyethyl)-3-aminopropiononitrile, N,N-bis(2-formyloxyethyl)-3-aminopropiononitrile, N,N-bis(2-methoxyethyl)-3-aminopropiononitrile, N,N-bis[2-(methoxymethoxy)ethyl]-3-aminopropiononitrile, methyl N-(2-cyanoethyl)-N-(2-methoxyethyl)-3-aminopropionate, methyl N-(2-cyanoethyl)-N-(2-hydroxyethyl)-3-aminopropionate, methyl N-(2-acetoxyethyl)-N-(2-cyanoethyl)-3-aminopropionate, N-(2-cyanoethyl)-N-ethyl-3-aminopropiononitrile, N-(2-cyanoethyl)-N-(2-hydroxyethyl)-3-aminopropiononitrile, N-(2-acetoxyethyl)-N-(2-cyanoethyl)-3-aminopropiononitrile, N-(2-cyanoethyl)-N-(2-formyloxyethyl)-3-aminopropiononitrile, N-(2-cyanoethyl)-N-(2-methoxyethyl)-3-aminopropiononitrile, N-(2-cyanoethyl)-N-[2-(methoxymethoxy)ethyl]-3-aminopropiononitrile, N-(2-cyanoethyl)-N-(3-hydroxy-1-propyl)-3-aminopropiononitrile, N-(3-acetoxy-1-propyl)-N-(2-cyanoethyl)-3-aminopropiononitrile, N-(2-cyanoethyl)-N-(3-formyloxy-1-propyl)-3-aminopropiononitrile, N-(2-cyanoethyl)-N-tetrahydrofurfuryl-3-aminopropiononitrile, N,N-bis(2-cyanoethyl)-3-aminopropiononitrile, diethylaminoacetonitrile, N,N-bis(2-hydroxyethyl)aminoacetonitrile, N,N-bis(2-acetoxyethyl)aminoacetonitrile, N,N-bis(2-formyloxyethyl)aminoacetonitrile, N,N-bis(2-methoxyethyl)aminoacetonitrile, N,N-bis[2-(methoxymethoxy)ethyl]aminoacetonitrile, methyl N-cyanomethyl-N-(2-methoxyethyl)-3-aminopropionate, methyl N-cyanomethyl-N-(2-hydroxyethyl)-3-aminopropionate, methyl N-(2-acetoxyethyl)-N-cyanomethyl-3-aminopropionate, N-cyanomethyl-N-(2-hydroxyethyl)aminoacetonitrile, N-(2-acetoxyethyl)-N-(cyanomethyl)aminoacetonitrile, N-cyanomethyl-N-(2-formyloxyethyl)aminoacetonitrile, N-cyanomethyl-N-(2-methoxyethyl)aminoacetonitrile, N-cyanomethyl-N-[2-(methoxymethoxy)ethyl)aminoacetonitrile, N-cyanomethyl-N-(3-hydroxy-1-propyl)aminoacetonitrile, N-(3-acetoxy-1-propyl)-N-(cyanomethyl)aminoacetonitrile, N-cyanomethyl-N-(3-formyloxy-1-propyl)aminoacetonitrile, N,N-bis(cyanomethyl)aminoacetonitrile, 1-pyrrolidinepropiononitrile, 1-piperidinepropiononitrile, 4-morpholinepropiononitrile, 1-pyrrolidineacetonitrile, 1-piperidineacetonitrile, 4-morpholineacetonitrile, cyanomethyl 3-diethylaminopropionate, cyanomethyl N,N-bis(2-hydroxyethyl)-3-aminopropionate, cyanomethyl N,N-bis(2-acetoxyethyl)-3-aminopropionate, cyanomethyl N,N-bis(2-formyloxyethyl)-3-aminopropionate, cyanomethyl N,N-bis(2-methoxyethyl)-3-aminopropionate, cyanomethyl N,N-bis[2-(methoxymethoxy)ethyl]-3-aminopropionate, 2-cyanoethyl 3-diethylaminopropionate, 2-cyanoethyl N,N-bis(2-hydroxyethyl)-3-aminopropionate, 2-cyanoethyl N,N-bis(2-acetoxyethyl)-3-aminopropionate, 2-cyanoethyl N,N-bis(2-formyloxyethyl)-3-aminopropionate, 2-cyanoethyl N,N-bis(2-methoxyethyl)-3-aminopropionate, 2-cyanoethyl N,N-bis[2-(methoxymethoxy)ethyl]-3-aminopropionate, cyanomethyl 1-pyrrolidinepropionate, cyanomethyl 1-piperidinepropionate, cyanomethyl 4-morpholinepropionate, 2-cyanoethyl 1-pyrrolidinepropionate, 2-cyanoethyl 1-piperidinepropionate, and 2-cyanoethyl 4-morpholinepropionate.

These basic compounds may be used alone or in admixture of any. The basic compound is preferably formulated in an amount of 0.001 to 2 parts, and especially 0.01 to 1 part by weight, per 100 parts by weight of the base resin. Less than 0.001 part of the basic compound may fail to achieve the desired effects thereof, while the use of more than 2 parts would result in too low a sensitivity.

Component (E)

The dissolution inhibitor (E) is preferably selected from compounds possessing a weight average molecular weight of 100 to 1,000 and having on the molecule at least two phenolic hydroxyl groups, in which an average of from 10 to 100 mol % of all the hydrogen atoms on the phenolic hydroxyl groups are replaced with acid labile groups.

Illustrative, non-limiting, examples of the dissolution inhibitor (E) which are useful herein include
bis(4-(2'-tetrahydropyranyloxy)phenyl)methane,
bis(4-(2'-tetrahydrofuranyloxy)phenyl)methane,
bis(4-tert-butoxyphenyl)methane,
bis(4-tert-butoxycarbonyloxyphenyl)methane,
bis(4-tert-butoxycarbonylmethyloxyphenyl)methane,
bis(4-(1'-ethoxyethoxy)phenyl)methane,
bis(4-(1'-ethoxypropyloxy)phenyl)methane,
2,2-bis(4'-(2''-tetrahydropyranyloxy))propane,
2,2-bis(4'-(2''-tetrahydrofuranyloxy)phenyl)propane,
2,2-bis(4'-tert-butoxyphenyl)propane,
2,2-bis(4'-tert-butoxycarbonyloxyphenyl)propane,
2,2-bis(4-tert-butoxycarbonylmethyloxyphenyl)propane,
2,2-bis(4'-(1''-ethoxyethoxy)phenyl)propane,
2,2-bis(4'-(1''-ethoxypropyloxy)phenyl)propane,
tert-butyl 4,4-bis(4'-(2''-tetrahydropyranyloxy)phenyl)valerate,
tert-butyl 4,4-bis(4'-(2''-tetrahydrofuranyloxy)phenyl)valerate,
tert-butyl 4,4-bis(4'-tert-butoxyphenyl)valerate,
tert-butyl 4,4-bis(4-tert-butoxycarbonyloxyphenyl)valerate,
tert-butyl 4,4-bis(4'-tert-butoxycarbonylmethyloxyphenyl)valerate,
tert-butyl 4,4-bis(4'-(1''-ethoxyethoxy)phenyl)valerate,
tert-butyl 4,4-bis(4'-(1''-ethoxypropyloxy)phenyl)valerate,
tris(4-(2'-tetrahydropyranyloxy)phenyl)methane,
tris(4-(2'-tetrahydrofuranyloxy)phenyl)methane,
tris(4-tert-butoxyphenyl)methane,
tris(4-tert-butoxycarbonyloxyphenyl)methane,
tris(4-tert-butoxycarbonyloxymethylphenyl)methane,
tris(4-(1'-ethoxyethoxy)phenyl)methane,
tris(4-(1'-ethoxypropyloxy)phenyl)methane,
1,1,2-tris(4'-(2''-tetrahydropyranyloxy)phenyl)ethane,
1,1,2-tris(4'-(2''-tetrahydrofuranyloxy)phenyl)ethane,
1,1,2-tris(4'-tert-butoxyphenyl)ethane,
1,1,2-tris(4'-tert-butoxycarbonyloxyphenyl)ethane,
1,1,2-tris(4'-tert-butoxycarbonylmethyloxyphenyl)ethane,
1,1,2-tris(4'-(1'-ethoxyethoxy)phenyl)ethane, and
1,1,2-tris(4'-(1'-ethoxypropyloxy)phenyl)ethane.

The compounds serving as dissolution inhibitor have a weight average molecular weight of 100 to 1,000, preferably 150 to 800.

An appropriate amount of the dissolution inhibitor (E) is 0 to about 50 parts, preferably about 5 to 50 parts, and especially about 10 to 30 parts by weight per 100 parts by weight of the base resin. Less amounts of the dissolution inhibitor may fail to yield an improved resolution, whereas too much amounts would lead to slimming of the patterned film, and thus a decline in resolution. The inhibitor may be used singly or as a mixture of two or more thereof.

The resist composition of the invention may include optional ingredients, typically a surfactant which is commonly used for improving the coating characteristics. Optional ingredients may be added in conventional amounts so long as this does not compromise the objects of the invention.

Illustrative, non-limiting, examples of the surfactant include nonionic surfactants, for example, polyoxyethylene alkyl ethers such as polyoxyethylene lauryl ether, polyoxyethylene stearyl ether, polyoxyethylene cetyl ether, and polyoxyethylene oleyl ether, polyoxyethylene alkylaryl ethers such as polyoxyethylene octylphenol ether and polyoxyethylene nonylphenol ether, polyoxyethylene polyoxypropylene block copolymers, sorbitan fatty acid esters such as sorbitan monolaurate, sorbitan monopalmitate, and sorbitan monostearate, and polyoxyethylene sorbitan fatty acid esters such as polyoxyethylene sorbitan monolaurate, polyoxyethylene sorbitan monopalmitate, polyoxyethylene sorbitan monostearate, polyoxyethylene sorbitan trioleate, and polyoxyethylene sorbitan tristearate; fluorochemical surfactants such as EFTOP EF301, EF303 and EF352 (Tohkem Products Co., Ltd.), Megaface F171, F172 and F173 (Dai-Nippon Ink & Chemicals, Inc.), Fluorad FC430 and FC431 (Sumitomo 3M Co., Ltd.), Asahiguard AG710, Surflon S-381, S-382, SC101, SC102, SC103, SC104, SC105, SC106, Surfynol E1004, KH-10, KH-20, KH-30 and KH-40 (Asahi Glass Co., Ltd.); organosiloxane polymers KP341, X-70-092 and X-70-093 (Shin-Etsu Chemical Co., Ltd.), acrylic acid or methacrylic acid Polyflow No. 75 and No. 95 (Kyoeisha Ushi Kagaku Kogyo Co., Ltd.). Inter alia, FC430, Surflon S-381, Surfynol E1004, KH-20 and KH-30 are preferred. These surfactants may be used alone or in admixture.

Pattern formation using the resist composition of the invention may be carried out by a known lithographic technique. For example, the resist composition may be applied onto a substrate such as a silicon wafer by spin coating or the like to form a resist film having a thickness of 0.1 to 1.0 µm, which is then pre-baked on a hot plate at 60 to 200° C. for 10 seconds to 10 minutes, and preferably at 80 to 150° C. for ½ to 5 minutes. A patterning mask having the desired pattern may then be placed over the resist film, and the film exposed through the mask to an electron beam or to high-energy radiation such as deep-UV rays, excimer laser beams, or x-rays in a dose of about 1 to 200 mJ/cm$^2$, and preferably about 10 to 100 mJ/cm$^2$, then post-exposure baked (PEB) on a hot plate at 60 to 150° C. for 10 seconds to 5 minutes, and preferably at 80 to 130° C. for ½ to 3 minutes. Finally, development may be carried out using as the developer an aqueous alkali solution, such as 0.1 to 5%, and preferably 2 to 3%, tetramethylammonium hydroxide (TMAH), this being done by a conventional method such as dipping, puddling, or spraying for a period of 10 seconds to 3 minutes, and preferably 30 seconds to 2 minutes. These steps result in the formation of the desired pattern on the substrate.

Of the various types of high-energy radiation that may be used, the resist composition of the invention is best suited to micro-pattern formation with, in particular, deep-UV rays having a wavelength of 254 to 120 nm, an excimer laser, especially ArF laser (193 nm), $F_2$ laser (157 nm), $Kr_2$ laser (146 nm), KrAr laser (134 nm) or $Ar_2$ laser (126 nm), x-rays, or an electron beam. Recommended is exposure to high-energy radiation in a wavelength band of 100 to 180 nm or 1 to 30 nm, specifically $F_2$ laser beam, $Ar_2$ laser beam or soft x-ray. The desired pattern may not be obtainable outside the upper and lower limits of the above range.

The resist composition of the invention is sensitive to high-energy radiation, maintains high transparency at a wavelength of up to 200 nm, and has improved alkali dissolution contrast and plasma etching resistance. These features permit the inventive resist composition to easily form a finely defined pattern having sidewalls perpendicular to the substrate and a high aspect ratio through $F_2$ laser exposure, making the resist ideal as a micropatterning material in VLSI fabrication.

EXAMPLE

Examples of the invention are given below by way of illustration and not by way of limitation. The abbreviations used herein are AIBN for 2,2'-azobisisobutyronitrile, GPC for gel permeation chromatography, NMR for nuclear magnetic resonance, Mw for weight average molecular weight, Mn for number average molecular weight, Mw/Mn for molecular weight distribution or dispersity, THF for tetrahydrofuran, and PGMEA for propylene glycol monomethyl ether acetate.

Monomer Synthesis Example 1

Synthesis of Monomer 1

Into a flask were admitted 40 g of dichloromethane, 10.0 g of Alcohol 1 shown below, and 13.0 g of pyridine. While the flask was immersed in an ice bath to keep the internal temperature below 10° C., 13.36 g of chloroethanesulfonyl chloride was added dropwise to the flask from a dropping funnel. The dropwise addition was followed by 2 hours of stirring. Conventional post treatment was carried out. The resulting oily matter was purified by silica gel chromatography, obtaining 10.9 g of Monomer 1. The yield was 64%.

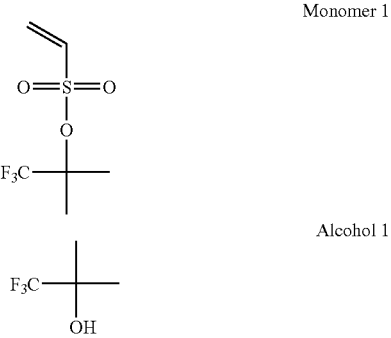

Monomer 1

Alcohol 1

Monomer Synthesis Example 2

Synthesis of Monomer 2

Into a flask were admitted 40 g of dichloromethane, 10.0 g of Alcohol 2 shown below, and 10.8 g of pyridine. While the flask was immersed in an ice bath to keep the internal temperature below 10° C., 11.11 g of chloroethanesulfonyl chloride was added dropwise to the flask from a dropping funnel. The dropwise addition was followed by 2 hours of stirring. Conventional post treatment was carried out. The resulting oily matter was purified by silica gel chromatography, obtaining 11.4 g of Monomer 2. The yield was 72%.

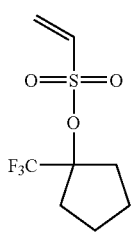

Monomer 2

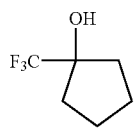

Alcohol 2

Polymer Synthesis Example 1

Copolymerization of Monomer 1, Monomer 3 and Monomer 4 (0.4:0.2:0.4)

A 300-ml flask was charged with 5.47 g of Monomer 1, 6.55 g of Monomer 3, shown below, and 7.98 g of Monomer 4, shown below, which were dissolved in 5.0 g of 1,4-dioxane. The system was fully purged of oxygen, charged with 0.51 g of the initiator AIBN, and heated at 65° C. at which polymerization reaction took place for 24 hours.

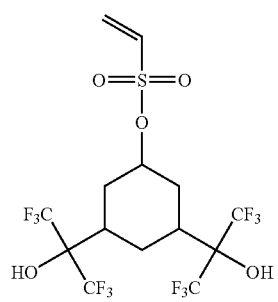

Monomer 3

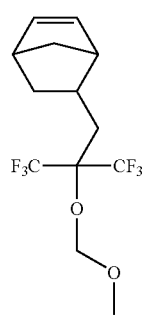

Monomer 4

The polymer thus obtained was worked up by pouring the reaction mixture into 1 liter of hexane whereupon the polymer precipitated. The procedure of dissolving the polymer in THF and pouring in 1 liter of hexane for precipitation was repeated twice, after which the polymer was separated and dried. There was obtained 12.5 g of a white polymer, which was found to have a Mw of 6,100 as measured by the light scattering method, and a dispersity (Mw/Mn) of 1.4 as determined from the GPC elution curve. On $^1$H-NMR analysis, the polymer was found to consist of respective units derived from Monomer 1, Monomer 3 and Monomer 4 in a molar ratio of 0.37:0.19:0.44.

Polymer Synthesis Example 2

Copolymerization of Monomer 1, Monomer 5 and Monomer 6 (0.3:0.3:0.4)

A 300-ml flask was charged with 5.60 g of Monomer 1, 5.03 g of Monomer 5, shown below, and 9.37 g of Monomer 6, shown below, which were dissolved in 5.0 g of 1,4-dioxane. The system was fully purged of oxygen, charged with 0.70 g of the initiator AIBN, and heated at 65° C. at which polymerization reaction took place for 24 hours.

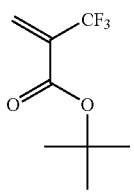

Monomer 5

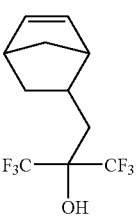

Monomer 6

The polymer thus obtained was worked up by pouring the reaction mixture into 1 liter of hexane whereupon the polymer precipitated. The procedure of dissolving the polymer in THF and pouring in 1 liter of hexane for precipitation was repeated twice, after which the polymer was separated and dried. There was obtained 11.7 g of a white polymer, which was found to have a Mw of 6,800 as measured by the light scattering method, and a dispersity (Mw/Mn) of 1.4 as determined from the GPC elution curve. On $^1$H-NMR analysis, the polymer was found to consist of respective units derived from Monomer 1, Monomer 5 and Monomer 6 in a molar ratio of 0.29:0.31:0.40.

Polymer Synthesis Example 3

Copolymerization of Monomer 1, Monomer 5 and Monomer 7 (0.3:0.3:0.4)

A 300-ml flask was charged with 4.38 g of Monomer 1, 3.94 g of Monomer 5 and 11.7 g of Monomer 7, shown below, which were dissolved in 5.0 g of 1,4-dioxane. The system was fully purged of oxygen, charged with 0.55 g of the initiator AIBN, and heated at 65° C. at which polymerization reaction took place for 24 hours.

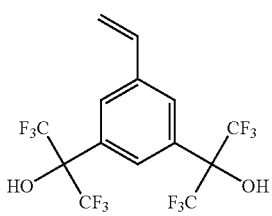

Monomer 7

The polymer thus obtained was worked up by pouring the reaction mixture into 1 liter of hexane whereupon the polymer precipitated. The procedure of dissolving the polymer in THF and pouring in 1 liter of hexane for precipitation was repeated twice, after which the polymer was separated and dried. There was obtained 12.9 g of a white polymer, which was found to have a Mw of 9,800 as measured by the light scattering method, and a dispersity (Mw/Mn) of 1.4 as determined from the GPC elution curve. On $^1$H-NMR analysis, the polymer was found to consist of respective units derived from Monomer 1, Monomer 5 and Monomer 7 in a molar ratio of 0.30:0.31:0.39.

Polymer Synthesis Example 4

Copolymerization of Monomer 2, Monomer 3 and Monomer 4 (0.4:0.2:0.4)

A 300-ml flask was charged with 5.93 g of Monomer 2, 6.34 g of Monomer 3 and 7.73 g of Monomer 4, which were dissolved in 5.0 g of 1,4-dioxane. The system was fully purged of oxygen, charged with 0.50 g of the initiator AIBN, and heated at 65° C. at which polymerization reaction took place for 24 hours.

The polymer thus obtained was worked up by pouring the reaction mixture into 1 liter of hexane whereupon the polymer precipitated. The procedure of dissolving the polymer in THF and pouring in 1 liter of hexane for precipitation was repeated twice, after which the polymer was separated and dried. There was obtained 13.9 g of a white polymer, which was found to have a Mw of 6,800 as measured by the light scattering method, and a dispersity (Mw/Mn) of 1.4 as determined from the GPC elution curve. On $^1$H-NMR analysis, the polymer was found to consist of respective units derived from Monomer 2, Monomer 3 and Monomer 4 in a molar ratio of 0.36:0.19:0.45.

Polymer Synthesis Example 5

Copolymerization of Monomer 2, Monomer 5 and Monomer 6 (0.3:0.3:0.4)

A 300-ml flask was charged with 6.06 g of Monomer 2, 4.87 g of Monomer 5 and 9.07 g of Monomer 6, which were dissolved in 5.0 g of 1,4-dioxane. The system was fully purged of oxygen, charged with 0.68 g of the initiator AIBN, and heated at 65° C. at which polymerization reaction took place for 24 hours.

The polymer thus obtained was worked up by pouring the reaction mixture into 1 liter of hexane whereupon the polymer precipitated. The procedure of dissolving the polymer in THF and pouring in 1 liter of hexane for precipitation was repeated twice, after which the polymer was separated and dried. There was obtained 14.2 g of a white polymer, which was found to have a Mw of 6,900 as measured by the light scattering method, and a dispersity (Mw/Mn) of 1.4 as determined from the GPC elution curve. On $^1$H-NMR analysis, the polymer was found to consist of respective units derived from Monomer 2, Monomer 5 and Monomer 6 in a molar ratio of 0.28:0.32:0.40.

Polymer Synthesis Example 6

Copolymerization of Monomer 2, Monomer 5 and Monomer 7 (0.3:0.3:0.4)

A 300-ml flask was charged with 4.78 g of Monomer 2, 3.84 g of Monomer 5 and 11.38 g of Monomer 7, which were dissolved in 5.0 g of 1,4-dioxane. The system was fully purged of oxygen, charged with 0.54 g of the initiator AIBN, and heated at 65° C. at which polymerization reaction took place for 24 hours.

The polymer thus obtained was worked up by pouring the reaction mixture into 1 liter of hexane whereupon the polymer precipitated. The procedure of dissolving the polymer in THF and pouring in 1 liter of hexane for precipitation was repeated twice, after which the polymer was separated and dried. There was obtained 13.6 g of a white polymer, which was found to have a Mw of 9,600 as measured by the light scattering method, and a dispersity (Mw/Mn) of 1.4 as determined from the GPC elution curve. On $^1$H-NMR analysis, the polymer was found to consist of respective units derived from Monomer 2, Monomer 5 and Monomer 7 in a molar ratio of 0.29:0.30:0.41.

Evaluation

Polymer Transmittance Measurement

The polymers obtained in Polymer Synthesis Examples 1 to 6, designated Polymers 1 to 6, respectively, were determined for transmittance. Three other polymers were furnished for comparison purposes. Comparative Polymer 1 is a monodisperse polyhydroxystyrene having a molecular weight of 10,000 and a dispersity (Mw/Mn) of 1.1 in which 30% of hydroxyl groups are replaced by tetrahydropyranyl groups. Similarly, Comparative Polymer 2 is polymethyl methacrylate having a molecular weight of 15,000 and a dispersity (Mw/Mn) of 1.7; and Comparative Polymer 3 is a novolac polymer having a meta/para ratio of 40/60, a molecular weight of 9,000 and a dispersity (Mw/Mn) of 2.5.

Each polymer, 1 g, was thoroughly dissolved in 20 g of PGMEA, and passed through a 0.2-μm filter, obtaining a polymer solution. The polymer solution was spin coated onto a MgF$_2$ substrate and baked on a hot plate at 100° C. for 90 seconds, forming a polymer film of 100 nm thick on the substrate. Using a vacuum ultraviolet spectrometer (VUV-200S by Nihon Bunko Co., Ltd.), the polymer film was measured for transmittance at 248 nm, 193 nm and 157 nm. The results are shown in Table 1.

TABLE 1

| | Transmittance (%) | | |
| --- | --- | --- | --- |
| | 248 nm | 193 nm | 157 nm |
| Polymer 1 | 99 | 93 | 72 |
| Polymer 2 | 99 | 93 | 67 |
| Polymer 3 | 99 | 10 | 63 |
| Polymer 4 | 99 | 93 | 71 |
| Polymer 5 | 99 | 93 | 66 |
| Polymer 6 | 99 | 10 | 62 |
| Comparative Polymer 1 | 90 | 5 | 15 |
| Comparative Polymer 2 | 91 | 80 | 12 |
| Comparative Polymer 3 | 82 | 6 | 17 |

It is evident from Table 1 that resist materials using the inventive polymers maintain sufficient transparency at the F$_2$ laser wavelength (157 nm).

Resist Preparation and Exposure

Resist solutions were prepared in a conventional manner by dissolving amounts as shown in Table 2 of the polymer, photoacid generator (PAG1 or PAG2), basic compound, and dissolution inhibitor (DRI1) in 1,000 parts of PGMEA.

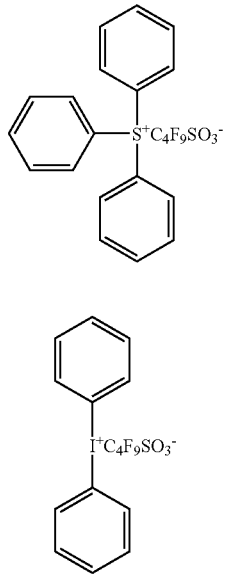

PAG1

PAG2

-continued

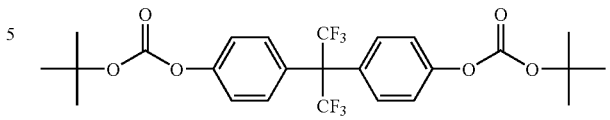

DRI1

On silicon wafers having a film of DUV-30 (Brewer Science) coated to a thickness of 85 nm, the resist solutions were spin coated, then baked on a hot plate at 120° C. for 90 seconds to give resist films having a thickness of 100 nm.

The resist films were exposed by means of an $F_2$ excimer laser exposure tool (VUVES-4500 by Litho Tech Japan Corp.) while varying the exposure dose. Immediately after exposure, the resist films were baked (PEB) at 120° C. for 90 seconds and then developed for 60 seconds with a 2.38% aqueous solution of tetramethylammonium hydroxide. The film thickness was measured in different dose areas. From the residual film thickness-to-dose relationship, the sensitivity (Eth) was determined as the exposure dose giving a film thickness 0. A γ value which was the slope (tan θ) of the characteristic curve was also determined.

Separately, through a mask having a Cr pattern formed on a $MgF_2$ substrate, the resist film in close contact with the Cr pattern surface was exposed to a $F_2$ laser for effecting contact exposure. The exposure was followed by similar PEB and development, forming a pattern. A cross section of the pattern was observed under SEM, the ascertainable minimum pattern size giving a resolution.

TABLE 2

| Polymer (pbw) | Photoacid generator (pbw) | Basic compound (pbw) | Dissolution inhibitor (pbw) | Solvent (pbw) | Eth, mJ/cm² | γ |
|---|---|---|---|---|---|---|
| Polymer 1 (100) | PAG1 (4) | tributylamine (0.1) | — | PGMEA (1000) | 18 | 8.9 |
| Polymer 2 (100) | PAG1 (4) | tributylamine (0.1) | — | PGMEA (1000) | 14 | 10.5 |
| Polymer 3 (100) | PAG1 (4) | tributylamine (0.1) | — | PGMEA (1000) | 12 | 10.9 |
| Polymer 4 (100) | PAG1 (4) | tributylamine (0.1) | — | PGMEA (1000) | 13 | 9.3 |
| Polymer 5 (100) | PAG1 (4) | tributylamine (0.1) | — | PGMEA (1000) | 11 | 10.8 |
| Polymer 6 (100) | PAG1 (4) | tributylamine (0.1) | — | PGMEA (1000) | 9 | 10.5 |
| Polymer 2 (100) | PAG1 (4) | triethanolamine (0.1) | — | PGMEA (1000) | 16 | 10.3 |
| Polymer 2 (100) | PAG1 (4) | tributylamine (0.1) | DRI1 (10) | PGMEA (1000) | 12 | 10.1 |
| Polymer 2 (100) | PAG2 (4) | tributylamine (0.1) | — | PGMEA (1000) | 10 | 12.9 |
| Comparative Polymer 1 (100) | PAG1 (4) | triethanolamine (0.1) | — | PGMEA (1000) | non-sensitive, turned negative without film thickness decreasing to 0 nm | — |

Upon exposure to VUVES, the resist compositions within the scope of the invention exhibited high gamma values and high contrast and exerted the positive working effect that the film thickness decreased with an increasing exposure dose. The resolving power upon contact exposure was high.

Dry Etching Test

A polymer solution was prepared by thoroughly dissolving 2 g of each of Polymers 1 to 6 in 10 g of PGMEA and passing the solution through a 0.2-micron size filter. The polymer solution was spin coated to a silicon substrate and baked to form a polymer film of 300 nm thick. The wafer having the polymer film formed thereon was subjected to dry etching under two sets of conditions. A first etching test with $CHF_3/CF_4$ gas was performed using a dry etching instrument TE-8500P by Tokyo Electron K.K. A second etching test with $Cl_2/BCl_3$ gas was performed using a dry etching instrument L-507D-L by Nichiden Anerba K.K. A difference in polymer film thickness before and after the etching test was determined. The etching conditions are shown in Table 3, and the results in Table 4.

TABLE 3

|  | $CHF_3/CF_4$ gas | $Cl_2/BCl_3$ gas |
| --- | --- | --- |
| Chamber pressure (Pa) | 40.0 | 40.0 |
| RF power (W) | 1,300 | 300 |
| Gap (mm) | 9 | 9 |
| Gas flow rate (ml/min) | $CHF_3$: 30 | $Cl_2$: 30 |
|  | $CF_4$: 30 | $BCl_3$: 30 |
|  | Ar: 100 | $CHF_3$: 100 |
|  |  | $O_2$: 2 |
| Time (sec) | 30 | 30 |

TABLE 4

| Polymer | $CHF_3/CF_4$ gas etching rate (nm/min) | $Cl_2/BCl_3$ gas etching rate (nm/min) |
| --- | --- | --- |
| Polymer 1 | 220 | 280 |
| Polymer 2 | 210 | 260 |
| Polymer 3 | 170 | 200 |
| Polymer 4 | 205 | 235 |
| Polymer 5 | 190 | 225 |
| Polymer 6 | 155 | 170 |

It is evident from Table 4 that the resist compositions within the scope of the invention are fully resistant to dry etching.

Japanese Patent Application No. 2003-032584 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A sulfonate compound having the following general formula (1):

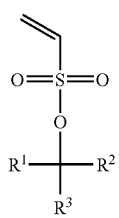

(1)

wherein $R^1$ to $R^3$ each are fluorine or a straight, branched or cyclic alkyl or fluorinated alkyl group of 1 to 20 carbon atoms, at least one of $R^1$ to $R^3$ contains fluorine, $R^1$ and $R^2$, $R^1$ and $R^3$, or $R^2$ and $R^3$, taken together, may form a ring, each of $R^1$ to $R^3$ is a straight or branched alkylene or fluorinated alkylene group of 1 to 18 carbon atoms, when they form a ring.

2. A polymer comprising recurring units of the following general formula (2) and having a weight average molecular weight of 1,000 to 500,000,

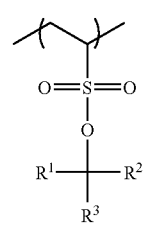

(2)

wherein $R^1$ to $R^3$ each are fluorine or a straight, branched or cyclic alkyl or fluorinated alkyl group of 1 to 20 carbon atoms, at least one of $R^1$ to $R^3$ contains fluorine, $R^1$ and $R^2$, $R^1$ and $R^3$, or $R^2$ and $R^3$, taken together, may form a ring, each of $R^1$ to $R^3$ is a straight or branched alkylene or fluorinated alkylene group of 1 to 18 carbon atoms, when they form a ring.

3. A polymer comprising recurring units of the following general formula (2) and recurring units of at least one type selected from the following general formulae (3a) to (3f) and having a weight average molecular weight of 1,000 to 500,000,

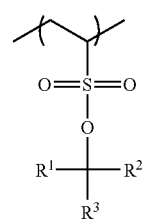

(2)

wherein $R^1$ to $R^3$ each are fluorine or a straight, branched or cyclic alkyl or fluorinated alkyl group of 1 to 20 carbon atoms, at least one of $R^1$ to $R^3$ contains fluorine, $R^1$ and $R^2$, $R^1$ and $R^3$ or $R^2$ and $R^3$, taken together, may form a ring, each of $R^1$ to $R^3$ is a straight or branched alkylene or fluorinated alkylene group of 1 to 18 carbon atoms, when they form a ring,

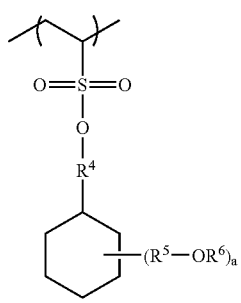

(3a)

-continued

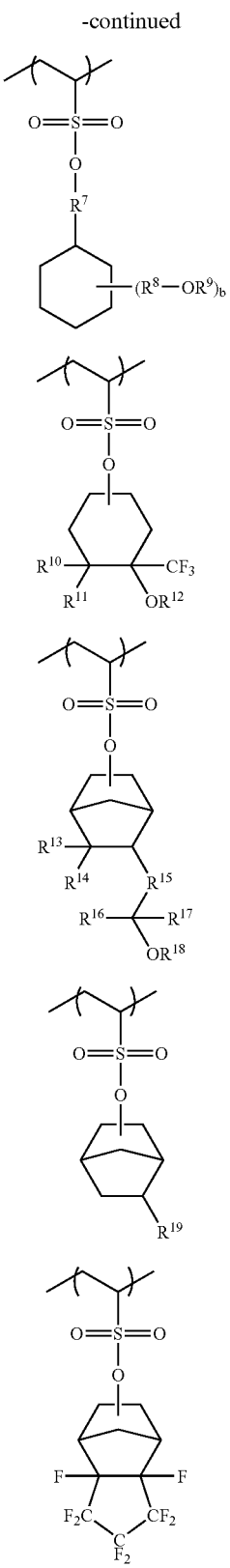

(3b)

(3c)

(3d)

(3e)

(3f)

wherein $R^4$, $R^5$, $R^7$, $R^8$ and $R^{15}$ each are a single bond or a straight, branched or cyclic alkylene or fluorinated alkylene group of 1 to 20 carbon atoms, $R^6$, $R^9$, $R^{12}$ and $R^{18}$ each are hydrogen or an acid labile group, $R^{10}$, $R^{11}$, $R^{13}$, $R^{14}$, $R^{16}$ and $R^{17}$ each are hydrogen, fluorine, a straight, branched or cyclic alkyl or fluorinated alkyl group of 1 to 20 carbon atoms, at least one of $R^{16}$ and $R^{17}$ contains at least one fluorine atom, $R^{19}$ is a straight, branched or cyclic fluorinated alkyl group of 1 to 20 carbon atoms, "a" and "b" each are 1 or 2.

4. A polymer comprising recurring units of the following general formula (2) and recurring units of the following general formula (4) and having a weight average molecular weight of 1,000 to 500,000,

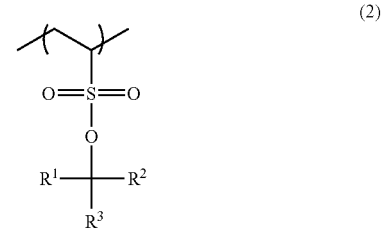

(2)

wherein $R^1$ to $R^3$ each are fluorine or a straight, branched or cyclic alkyl or fluorinated alkyl group of 1 to 20 carbon atoms, at least one of $R^1$ to $R^3$ contains fluorine, $R^1$ and $R^2$, $R^1$ and $R^3$, or $R^2$ and $R^3$, taken together, may form a ring, each of $R^1$ to $R^3$ is a straight or branched alkylene or fluorinated alkylene group of 1 to 18 carbon atoms, when they form a ring,

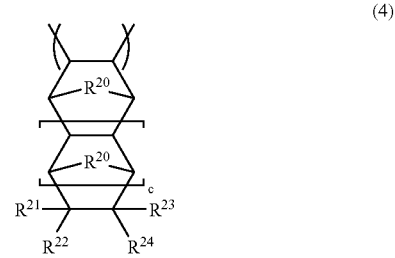

(4)

wherein $R^{20}$ is a methylene group, oxygen atom or sulfur atom, $R^{21}$ to $R^{24}$ each are hydrogen, fluorine, —$R^{25}$—$OR^{26}$, —$R^{25}$—$CO_2R^{26}$ or a straight, branched or cyclic alkyl or fluorinated alkyl group of 1 to 20 carbon atoms, at least one of $R^{21}$ to $R^{24}$ containing —$R^{25}$—$OR^{26}$ or —$R^{25}CO_2R^{26}$, $R^{25}$ is a single bond or a straight, branched or cyclic alkylene or fluorinated alkylene group of 1 to 20 carbon atoms, $R^{26}$ is hydrogen, an acid labile group, adhesive group or a straight, branched or cyclic fluorinated alkyl group of 1 to 20 carbon atoms which may contain a hydrophilic group,3 and c is 0 or 1.

5. The polymer of claim 4 wherein said recurring units of formula (4) have a structure of the following general formula (4a) or (4b):

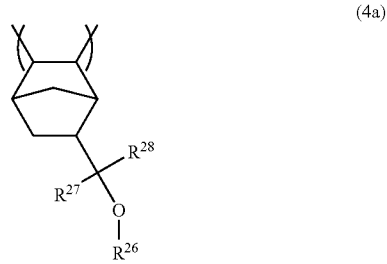

(4a)

-continued

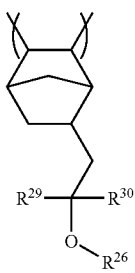
(4b)

wherein $R^{26}$ is as defined above, $R^{27}$ to $R^{30}$ each are hydrogen, fluorine or an alkyl or fluorinated alkyl group of 1 to 4 carbon atoms, at least either one of $R^{27}$ and $R^{28}$ contains at least one fluorine atom, and at least either one of $R^{29}$ and $R^{30}$ contains at least one fluorine atom.

6. A polymer comprising recurring units of the following general formula (2) and recurring units of at the following general formula (5) and having a weight average molecular weight of 1,000 to 500,000,

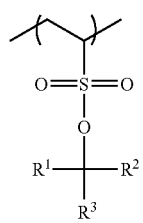
(2)

wherein $R^1$ to $R^3$ each are fluorine or a straight, branched or cyclic alkyl or fluorinated alkyl group of 1 to 20 carbon atoms, at least one of $R^1$ to $R^3$ contains fluorine, $R^1$ and $R^2$, $R^1$ and $R^3$ or $R^2$ and $R^3$, taken together, may form a ring, each of $R^1$ to $R^3$ is a straight or branched alkylene or fluorinated alkylene group of 1 to 18 carbon atoms, when they form a ring,

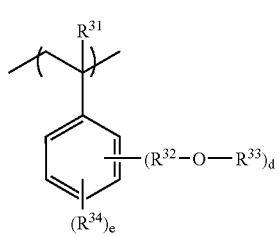
(5)

wherein $R^{31}$ is hydrogen, fluorine or a straight, branched or cyclic alkyl or fluorinated alkyl group of 1 to 20 carbon atoms, $R^{32}$ is a single bond or a straight, branched or cyclic alkylene or fluorinated alkylene group of 1 to 20 carbon atoms, $R^{33}$ is hydrogen or an acid labile group, $R^{34}$ is fluorine or a straight, branched or cyclic fluorinated alkyl group of 1 to 20 carbon atoms, d is 1 or 2, and e is an integer of 0 to 4, satisfying $1 \leq d+e \leq 5$.

7. The polymer of claim 6 wherein the recurring units of formula (5) have the following formula (5a) or (5b):

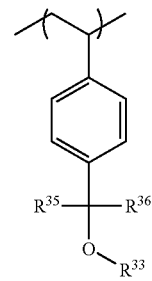
(5a)

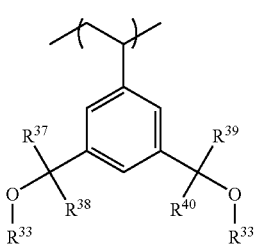
(5b)

wherein $R^{33}$ is as defined above, $R^{35}$ to $R^{40}$ each are hydrogen, fluorine or an alkyl or fluorinated alkyl group of 1 to 4 carbon atoms, at least either one of $R^{35}$ and $R^{36}$ contains at least one fluorine atom, at least either one of $R^{37}$ and $R^{38}$ contains at least one fluorine atom, and at least either one of $R^{39}$ and $R^{40}$ contains at least one fluorine atom.

8. A polymer comprising recurring units of the following general formula (2) and recurring units of the following general formula (6) and having a weight average molecular weight of 1,000 to 500,000,

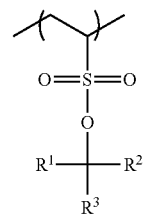
(2)

wherein $R^1$ to $R^3$ each are fluorine or a straight, branched or cyclic alkyl or fluorinated alkyl group of 1 to 20 carbon atoms, at least one of $R^1$ to $R^3$ contains fluorine, $R^1$ and $R^2$, $R^1$ and $R^3$, or $R^2$ and $R^3$, taken together, may form a ring, each of $R^1$ to $R^3$ is a straight or branched alkylene or fluorinated alkylene group of 1 to 18 carbon atoms, when they form a ring,

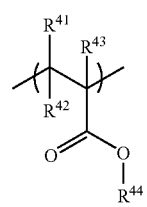
(6)

wherein $R^{41}$ to $R^{43}$ each are hydrogen, fluorine or a straight, branched or cyclic alkyl or fluorinated alkyl group of 1 to 20 carbon atoms, and $R^{44}$ is hydrogen, an acid labile group, an adhesive group or a straight, branched or cyclic fluorinated alkyl group of 1 to 20 carbon atoms which may contain a hydrophilic group such as hydroxyl.

9. The polymer of claim 8 wherein $R^{43}$ in formula (6) is trifluoromethyl.

10. A resist composition comprising the polymer of claim 2.

11. A chemically amplified positive resist composition comprising
    (A) the polymer of claim 2,
    (B) an organic solvent, and
    (C) a photoacid generator.

12. The resist composition of claim 11, further comprising (D) a basic compound.

13. The resist composition of claim 11, further comprising (E) a dissolution inhibitor.

14. A process for forming a resist pattern comprising the steps of:
    applying the resist composition of claim 10 onto a substrate to form a coating,
    heat treating the coating and then exposing it to high-energy radiation in a wavelength band of 100 to 180 nm or 1 to 30 nm through a photomask, and
    optionally heat treating the exposed coating and developing it with a developer.

15. The pattern forming process of claim 14 wherein the high-energy radiation is an $F_2$ laser beam, $Ar_2$ laser beam or soft x-ray.

16. A chemically amplified positive resist composition comprising
    (A) the polymer of claim 3,
    (B) an organic solvent, and
    (C) a photoacid generator.

17. A chemically amplified positive resist composition comprising
    (A) the polymer of claim 4,
    (B) an organic solvent, and
    (C) a photoacid generator.

18. A chemically amplified positive resist composition comprising
    (A) the polymer of claim 6,
    (B) an organic solvent, and
    (C) a photoacid generator.

19. A chemically amplified positive resist composition comprising
    (A) the polymer of claim 8,
    (B) an organic solvent, and
    (C) a photoacid generator.

* * * * *